US011060121B2

(12) United States Patent
Smirnov et al.

(10) Patent No.: US 11,060,121 B2
(45) Date of Patent: Jul. 13, 2021

(54) METHOD OF PRODUCING GLYCINE BY FERMENTATION

(71) Applicant: AJINOMOTO CO., INC., Tokyo (JP)

(72) Inventors: Sergey Vasilievich Smirnov, Moscow (RU); Veronika Aleksandrovna Kotliarova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/909,139

(22) Filed: Jun. 23, 2020

(65) Prior Publication Data

US 2020/0325507 A1 Oct. 15, 2020

Related U.S. Application Data

(63) Continuation of application No. PCT/JP2018/038012, filed on Sep. 28, 2018.

(30) Foreign Application Priority Data

Dec. 26, 2017 (RU) .......................... RU2017146016

(51) Int. Cl.
*C12P 13/04* (2006.01)
*C12N 9/10* (2006.01)
*C12N 9/02* (2006.01)
*C12N 9/04* (2006.01)

(52) U.S. Cl.
CPC ............. *C12P 13/04* (2013.01); *C12N 9/0006* (2013.01); *C12N 9/1029* (2013.01); *C12Y 101/01103* (2013.01); *C12Y 203/01029* (2013.01)

(58) Field of Classification Search
CPC ........ C12N 15/77; C12N 9/88; C12N 9/2437; C12N 9/0061; C12N 9/0065; C07K 14/34; C12P 13/04; C12P 13/08
See application file for complete search history.

(56) References Cited

U.S. PATENT DOCUMENTS

| 4,278,765 A | 7/1981 | Debabov et al. |
| 4,346,170 A | 8/1982 | Sano et al. |
| 5,661,012 A | 8/1997 | Sano et al. |
| 5,965,391 A | 10/1999 | Reinscheid et al. |
| 6,040,160 A | 3/2000 | Kojima et al. |
| 9,024,113 B2 * | 5/2015 | Cao .................... C12N 15/8274 800/298 |
| 2006/0216796 A1 | 9/2006 | Hashiguchi et al. |

FOREIGN PATENT DOCUMENTS

| EP | 0685555 A1 | 12/1995 |
| EP | 1243657 B1 | 9/2002 |
| WO | WO95/16042 A1 | 6/1995 |
| WO | WO96/15246 A1 | 5/1996 |

OTHER PUBLICATIONS

Newman et al., J. Bacteriol., 1976, 126(3), 1245-1249.*
Liu et al., Crit. Rev. Biotechnol., pp. 1-13, Feb. 2015, published online.*
Lin, Z., et al., "Metabolic engineering of *Escherichia coli* for poly(3-hydroxybutyrate) production via threonine bypass," Microb. Cell Fact. 2015;14:185 (12 pp.).
Marcus, J. P., et al., "Threonine Formation via the Coupled Activity of 2-Amino-3-Ketobutyrate Coenzyme A Lyase and Threonine Dehydrogenase," J. Bacteriol. 1993;175(20):6505-6511.
Zou, Y., et al., "Enhancement of 5-aminolevulinic acid production by metabolic engineering of the glycine biosynthesis pathway in *Corynebacterium glutamicum*," Biotechnol. Lett. 2017;39:1369-1374.
Schweitzer, J.-E., et al., "The serine hydroxymethyltransferase gene glyA in *Corynebacterium glutamicum* in controlled by GlyR," J. Biotechnol. 2009;139:214-221.
"Glycine From Japan and Korea," Investigation Nos. 731-TA-1112 and 1113 (Final), U.S. International Trade Commission, Publication 3980, Jan. 2008, 140 pp.
International Search Report for PCT Patent App. No. PCT/JP2018/038012 (dated Jan. 10, 2019).
Written Opinion for PCT Patent App. No. PCT/JP2018/038012 (dated Jan. 10, 2019).

* cited by examiner

*Primary Examiner* — Maryam Monshipouri
(74) *Attorney, Agent, or Firm* — Cermak Nakajima & McGowan LLP; Shelly Guest Cermak

(57) ABSTRACT

The present invention provides a method for producing glycine or a salt thereof by fermentation of a bacterium which has been modified to overexpress a gene encoding a protein having L-threonine 3-dehydrogenase activity and a gene encoding a protein having 2-amino-3-oxobutanoate coenzyme A ligase activity. The bacterium can be, for example, a coryneform bacterium or a bacterium belonging to the family Enterobacteriaceae.

7 Claims, 4 Drawing Sheets

Specification includes a Sequence Listing.

METHOD OF PRODUCING GLYCINE BY FERMENTATION

This application is a continuation of, and claims priority under 35 U.S.C. § 120 to, International Application No. PCT/JP2018/038012, filed Sep. 28, 2018, and claims priority therethrough under 35 U.S.C. § 119 to Japanese Patent Application No. 2017-146016, filed Dec. 26, 2017, the entireties of which are incorporated by reference herein. Also, the Sequence Listing filed electronically herewith is hereby incorporated by reference (File name: 2020-06-23_US-611_Seq_List; File size: 15 KB; Date recorded: Jun. 23, 2020).

BACKGROUND

General Field

The present invention relates to the microbiological industry, and specifically to a method of producing glycine by fermentation of a bacterium, which may be a coryneform bacterium or a bacterium belonging to the family Enterobacteriaceae, which has been modified to overexpress a gene encoding a protein having L-threonine 3-dehydrogenase activity and a gene encoding a protein having 2-amino-3-oxobutanoate coenzyme A ligase activity, so that glycine can be produced by a non-chemical technique.

DESCRIPTION OF THE RELATED ART

Conventionally, amino acids such as L-amino acids are industrially produced by fermentation methods utilizing strains of microorganisms obtained from natural sources, or mutants thereof. Typically, the microorganisms are modified to enhance production yields of amino acids.

Many techniques to enhance L-amino acids production yields have been reported, including transformation of microorganisms with recombinant DNA (see, for example, U.S. Pat. No. 4,278,765 A) and alteration of expression regulatory regions such as promoters, leader sequences, and/or attenuators, or others known to the person of ordinary skill in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes which are involved in degradation of the target L-amino acid, genes which divert the precursors of the target L-amino acid from the L-amino acid biosynthetic pathway, genes involved in the redistribution of the carbon, nitrogen, and phosphate fluxes, and genes encoding toxins, etc.

Glycine is a conditionally essential amino acid for humans and other animals, meaning that the synthesis of glycine can be limited under specific physiological conditions such as, for example, metabolic disorder-related diseases. It is required by the body for the maintenance of the central nervous system and immune system. Glycine is used in the food industry as a preservative, an antioxidant, and a browning and seasoning agent. As it has a sweet taste, it can enhance the taste of saccharin and mask the bitter aftertaste of intense sweeteners. The Maillard reaction between amino acids and reducing sugars is known to give the roasted and baked food products the distinctive browning and flavor development. Glycine is used specifically for this purpose. Glycine is used also as a chelating agent towards metal ions to suppress auto-oxidative reactions and growth of bacteria in media. However, it has little preservative activity against molds and yeast.

Glycine is a unique proteinogenic amino acid as it is achiral. Therefore, glycine is produced mainly using chemical means (that is, synthetically). Methods for producing glycine are known, and these include the hydrogen cyanide process (so-called HCN process, Strecker's reaction) and the monochloroacetic acid process (so-called MCA process) (Glycine From Japan and Korea; Investigation Nos. 731-TA-1112 and 1113 (Final); U.S. International Trade Commission, Publication 3980, January 2008). In the HCN process, hydrogen cyanide and formaldehyde are utilized as the starting materials. In the MCA process, glycine is synthesized from monochloroacetic acid and ammonia. Also, a method for producing glycine from glycinonitrile using a hydrolysis reaction under the action of a microbial enzyme having the activity of hydrolyzing nitrile group and native to bacterial or fungal species is known (EP1243657 B1).

Glycine at three grades of purity is available typically on the market, that is, the glycine of pharmaceutical grade, USP (United States Pharmacopeia) grade, and technical grade. The glycine at these grades of purity is chemically identical, however, the kind and amounts of impurities vary in glycine preparations depending on the grade of purity. As glycine is utilized in various industrial fields, including the pharmaceutical industry and food processing industry, the glycine produced using non-chemical methods and at a high grade of purity at reasonable price is in demand.

However, a method for production of glycine by fermentation of a bacterium such as, for example, a coryneform bacterium or a bacterium belonging to the family Enterobacteriaceae is not known, let alone a method of producing glycine by fermentation of a bacterium, which has been modified to overexpress a gene encoding a protein having L-threonine 3-dehydrogenase activity and a gene encoding a protein having 2-amino-3-oxobutanoate coenzyme A ligase activity.

SUMMARY

A novel method of producing glycine by fermentation of a bacterium is described herein. According to the presently disclosed subject matter, a coryneform bacterium or a bacterium belonging to the family Enterobacteriaceae such as, for example, a bacterium of the genera *Corynebacterium* and *Escherichia*, can be engineered to be able to produce glycine by fermentation of the bacterium. Specifically, a coryneform bacterium or a bacterium belonging to the family Enterobacteriaceae can be engineered to be able to produce glycine by fermentation of the bacterium, when the bacterium has been modified to overexpress a gene encoding a protein having L-threonine 3-dehydrogenase activity and a gene encoding a protein having 2-amino-3-oxobutanoate coenzyme A ligase activity. Also, production of glycine by fermentation of a bacterium that may be a coryneform bacterium or a bacterium belonging to the family Enterobacteriaceae such as, for example, a bacterium of the genera *Corynebacterium* and *Escherichia* can be improved by overexpressing a gene encoding a protein having L-threonine 3-dehydrogenase activity and a gene encoding a protein having 2-amino-3-oxobutanoate coenzyme A ligase activity in the bacterium so that the production of glycine by the modified bacterium can be improved as compared with a non-modified strain. Therefore, glycine can be produced according to the method described herein by fermentation of the bacterium modified as described herein.

A coryneform bacterium or a bacterium belonging to the family Enterobacteriaceae can become able to produce glycine in a culture medium when the bacterium is cultivated in the culture medium so that the glycine can be produced by the bacterium and collected from the medium, when the bacterium has been modified to overexpress the gene encoding a protein having L-threonine 3-dehydrogenase activity and the gene encoding a protein having 2-amino-3-oxobutanoate coenzyme A ligase activity. For example, a bacterium of the genera *Corynebacterium* and *Escherichia* can be engineered to be able to produce glycine in the culture medium when the bacterium is cultivated in the culture medium so that the glycine can be produced by the bacterium and collected from the medium, when the bacterium has been modified to overexpress the tdh gene and the kbl gene. That is, the ability to produce glycine can be conferred on a bacterium by modifying the bacterium in such a way that the gene encoding a protein having L-threonine 3-dehydrogenase activity and the gene encoding a protein having 2-amino-3-oxobutanoate coenzyme A ligase activity are overexpressed, such that when the bacterium is cultivated in the culture medium the glycine can be produced by the bacterium and collected from the medium.

It is one aspect of the present invention to provide a method for producing glycine or a salt thereof comprising: (i) cultivating a glycine-producing bacterium in a culture medium to produce and accumulate the glycine or a salt thereof in the culture medium or the bacterial cells, or both; and (ii) collecting the glycine or the salt thereof from the culture medium or the bacterial cells, or both, wherein the bacterium has been modified to overexpress a gene encoding a protein having L-threonine 3-dehydrogenase activity and a gene encoding a protein having 2-amino-3-oxobutanoate coenzyme A ligase activity.

It is a further aspect of the present invention to provide the method as described above, wherein said protein having L-threonine 3-dehydrogenase activity is encoded by a tdh gene and said protein having 2-amino-3-oxobutanoate coenzyme A ligase activity is encoded by a kbl gene.

It is a further aspect of the present invention to provide the method as described above, wherein said protein having L-threonine 3-dehydrogenase activity is selected from the group consisting of: (A) a protein comprising the amino acid sequence shown in SEQ ID NO: 2, (B) a protein comprising the amino acid sequence shown in SEQ ID NO: 2, but which includes substitution, deletion, insertion, and/or addition of 1 to 50 amino acid residues, and wherein said protein has L-threonine 3-dehydrogenase activity, (C) a protein having an identity of amino acid residues of not less than 60% with respect to the entire amino acid sequence shown in SEQ ID NO: 2, and wherein said protein has L-threonine 3-dehydrogenase activity; and wherein said protein having 2-amino-3-oxobutanoate coenzyme A ligase activity is selected from the group consisting of: (D) a protein comprising the amino acid sequence shown in SEQ ID NO: 4, (E) a protein comprising the amino acid sequence shown in SEQ ID NO: 4, but which includes substitution, deletion, insertion, and/or addition of 1 to 50 amino acid residues, and wherein said protein has 2-amino-3-oxobutanoate coenzyme A ligase activity, (F) a protein having an identity of amino acid residues of not less than 60% with respect to the entire amino acid sequence shown in SEQ ID NO: 4, and wherein said protein has 2-amino-3-oxobutanoate coenzyme A ligase activity.

It is a further aspect of the present invention to provide the method as described above, wherein said protein having L-threonine 3-dehydrogenase activity is encoded by a DNA selected from the group consisting of: (a) a DNA comprising the nucleotide sequence shown in SEQ ID NO: 1, (b) a DNA encoding a protein comprising the amino acid sequence shown in SEQ ID NO: 2, but which includes substitution, deletion, insertion, and/or addition of 1 to 50 amino acid residues, and wherein said protein has L-threonine 3-dehydrogenase activity, (c) a DNA which is a variant nucleotide sequence of SEQ ID NO: 1 due to the degeneracy of the genetic code; and wherein said protein having 2-amino-3-oxobutanoate coenzyme A ligase is encoded by a DNA selected from the group consisting of: (d) a DNA comprising the nucleotide sequence shown in SEQ ID NO: 3, (e) a DNA encoding a protein comprising the amino acid sequence shown in SEQ ID NO: 4, but which includes substitution, deletion, insertion and/or addition of 1 to 50 amino acid residues, and wherein said protein has 2-amino-3-oxobutanoate coenzyme A ligase activity, (f) a DNA which is a variant nucleotide sequence of SEQ ID NO: 3 due to the degeneracy of the genetic code.

It is a further aspect of the present invention to provide the method as described above, wherein the gene encoding the protein having L-threonine 3-dehydrogenase activity and the gene encoding the protein having 2-amino-3-oxobutanoate coenzyme A ligase activity are overexpressed by introducing the genes, increasing the copy number of the genes, or by modifying an expression regulatory region of the genes, or a combination of these, so that the expression of said genes is enhanced as compared with a non-modified bacterium.

It is a further aspect of the present invention to provide the method as described above, wherein said bacterium is a coryneform bacterium or a bacterium belonging to the family Enterobacteriaceae.

It is a further aspect of the present invention to provide the method as described above, wherein said coryneform bacterium belongs to the genus *Corynebacterium* or *Brevibacterium*.

It is a further aspect of the present invention to provide the method as described above, wherein said coryneform bacterium is *Corynebacterium glutamicum*.

It is a further aspect of the present invention to provide the method as described above, wherein said bacterium belonging to the family Enterobacteriaceae belongs to the genus *Escherichia* or *Pantoea*.

It is a further aspect of the present invention to provide the method as described above, wherein said bacterium belonging to the family Enterobacteriaceae is *Escherichia coli* or *Pantoea ananatis*.

It is another aspect of the present invention to provide a glycine-producing bacterium, wherein said bacterium has been modified to overexpress a gene encoding a protein having L-threonine 3-dehydrogenase activity and a gene encoding a protein having 2-amino-3-oxobutanoate coenzyme A ligase activity.

It is a further aspect of the present invention to provide the bacterium as described above, wherein said protein having L-threonine 3-dehydrogenase activity is selected from the group consisting of: (A) a protein comprising the amino acid sequence shown in SEQ ID NO: 2, (B) a protein comprising the amino acid sequence shown in SEQ ID NO: 2, but which includes substitution, deletion, insertion, and/or addition of 1 to 50 amino acid residues, and wherein said protein has L-threonine 3-dehydrogenase activity, (C) a protein having an identity of amino acid residues of not less than 60% with respect to the entire amino acid sequence shown in SEQ ID NO: 2, and wherein said protein has L-threonine 3-dehydrogenase activity; and wherein said protein having 2-amino-3-oxobutanoate coenzyme A ligase activity is selected from the group consisting of: (D) a protein comprising the amino acid sequence shown in SEQ ID NO: 4, (E) a protein comprising the amino acid sequence shown in SEQ ID NO: 4, but which includes substitution, deletion, insertion, and/or addition of 1 to 50 amino acid residues, and wherein said protein has 2-amino-3-oxobutanoate coenzyme A ligase activity, (F) a protein having an identity of amino acid residues of not less than 60% with respect to the entire amino acid sequence shown in SEQ ID NO: 4, and wherein said protein has 2-amino-3-oxobutanoate coenzyme A ligase activity.

It is a further aspect of the present invention to provide the bacterium as described above, wherein said bacterium has been modified to overexpress a tdh gene and a kbl gene.

It is a further aspect of the present invention to provide the bacterium as described above, wherein the gene encoding the protein having L-threonine 3-dehydrogenase activity and the gene encoding the protein having 2-amino-3-oxobutanoate coenzyme A ligase activity are overexpressed by introducing the genes, increasing the copy number of the genes, or by modifying an expression regulatory region of the genes, or a combination of these, so that the expression of said genes is enhanced as compared with a non-modified bacterium.

It is a further aspect of the present invention to provide the bacterium as described above, wherein said bacterium is a coryneform bacterium or a bacterium belonging to the family Enterobacteriaceae.

It is a further aspect of the present invention to provide the bacterium as described above, wherein said coryneform bacterium belongs to the genus *Corynebacterium* or *Brevibacterium*.

It is a further aspect of the present invention to provide the bacterium as described above, wherein said coryneform bacterium is *Corynebacterium glutamicum*.

It is a further aspect of the present invention to provide the bacterium as described above, wherein said bacterium belonging to the family Enterobacteriaceae belongs to the genus *Escherichia* or *Pantoea*.

It is a further aspect of the present invention to provide the bacterium as described above, wherein said bacterium belonging to the family Enterobacteriaceae is *Escherichia coli* or *Pantoea ananatis*.

The present invention is described in detail below.

DETAILED DESCRIPTION

1. Bacterium

Figure 1A:
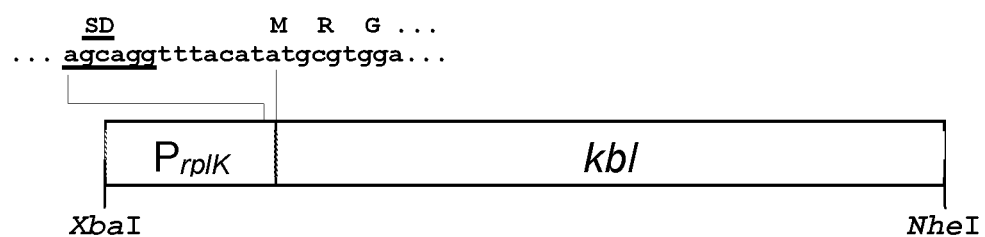
FIGS. 1A and 1B show the structure of the DNA fragments <KBL> (A) and <TDH> (B). $P_{rplK}$— promoter of rplK gene, $P_{gapA}$—promoter of gapA gene, SD—Shine-Dalgarno sequence.

In a method as described herein, any bacterium that can be modified to overexpress a gene encoding a protein having L-threonine 3-dehydrogenase activity and a gene encoding a protein having 2-amino-3-oxobutanoate coenzyme A ligase activity can be used so long as the bacterium thus modified is able to produce glycine by fermentation of the bacterium in a culture medium. Alternatively, any bacterium can be used so long as the bacterium is able to produce glycine by fermentation when the bacterium has been modified to overexpress the gene encoding a protein having L-threonine 3-dehydrogenase activity and the gene encoding a protein having 2-amino-3-oxobutanoate coenzyme A ligase activity. The bacterium as described herein can be a glycine-producing bacterium modified to overexpress the gene encoding a protein having L-threonine 3-dehydrogenase activity and the gene encoding a protein having 2-amino-3-oxobutanoate coenzyme A ligase activity. Examples of the bacterium are described hereinafter.

The phrase "a bacterium is able to produce glycine" after introducing a modification can mean that the bacterium, previously not having an ability to produce glycine, can obtain the ability to produce glycine after introducing such modification. Also, the phrase "a bacterium is able to produce glycine" after introducing a modification can mean that the bacterium is rendered able to produce glycine after introducing the modification such that the modified bacterium is able to produce glycine.

The phrase "a glycine-producing bacterium" can mean a bacterium which is able to produce, excrete or secrete, and/or cause accumulation of glycine in a culture medium and/or the bacterial cells when the bacterium is cultivated in the medium. The phrase "a bacterium is cultivated in a medium" can be equivalent to the phrase "a bacterium is cultured in a medium", and these phrases are known to persons of ordinary skill in the art. The phrase "a glycine-producing bacterium" can also mean a bacterium which is able to produce, excrete or secrete, and/or cause accumulation of glycine in a culture medium in an amount larger than a non-modified strain, for example, a wild-type or parental strain such as *Corynebacterium glutamicum* (*C. glutamicum*) ATCC13032 or *Escherichia coli* (*E. coli*) K-12. The bacterium can cause accumulation in the medium of an amount not less than 0.01 g/L of the target glycine, for example, not less than 0.1 g/L, or not less than 0.5 g/L, or not less than 1.0 g/L of the target glycine.

The phrase "a bacterium is able to produce glycine" can mean that the bacterium is can produce, excrete or secrete, and/or cause accumulation of glycine in a culture medium and/or the bacterial cells to such a level that the glycine can be collected from the culture medium and/or the bacterial cells when the bacterium is cultivated in the medium. The phrase "a bacterium is able to produce glycine" can also mean that the bacterium can produce, excrete or secrete, and/or cause accumulation of glycine in a culture medium and/or the bacterial cells to such the level that an amount of the target glycine in the medium and/or the bacterial cells is not less than 0.01 g/L.

The bacterium can produce glycine or a salt thereof, or a mixture of them. Therefore, the phrase "glycine" can include not only glycine in a free form, but may also include a salt or hydrate of the glycine, or an adduct formed by the glycine and another organic or inorganic compound. It is also acceptable that the bacterium can produce glycine either alone or as a mixture of the glycine and one or more kinds of other amino acids, for example, L-amino acids that are different from the target glycine. The phrase "L-amino acid" can mean an amino acid in L-form (so-called L-enantiomer of an amino acid) such as L-alanine, L-arginine, L-asparagine, L-aspartic acid, L-citrulline, L-cysteine, L-glutamic acid, L-glutamine, L-histidine, L-isoleucine, L-leucine, L-lysine, L-methionine, L-ornithine, L-phenylalanine, L-proline, L-serine, L-threonine, L-tryptophan, L-tyrosine, and L-valine.

Furthermore, a bacterium modified to overexpress a gene encoding a protein having L-threonine 3-dehydrogenase activity and a gene encoding a protein having 2-amino-3-oxobutanoate coenzyme A ligase activity, which is able to produce glycine, can also be used. The bacterium may inherently be able to produce glycine or may be modified to become able to produce glycine by using a mutation method or DNA recombination techniques. That is, the bacterium can be obtained by overexpressing a gene encoding a protein having L-threonine 3-dehydrogenase activity and a gene encoding a protein having 2-amino-3-oxobutanoate coenzyme A ligase activity in a bacterium that inherently is able to produce glycine. Alternatively, the bacterium can be obtained by overexpressing a gene encoding a protein having L-threonine 3-dehydrogenase activity and a gene encoding a protein having 2-amino-3-oxobutanoate coenzyme A ligase activity to render the bacterium able to produce glycine. That is, the bacterium can be modified to overexpress the gene encoding a protein having L-threonine 3-dehydrogenase activity and the gene encoding a protein having 2-amino-3-oxobutanoate coenzyme A ligase activity so that the bacterium thus modified can become able to produce glycine.

A bacterium as described herein can be, for example, a gram-positive bacterium or a gram-negative bacterium, specific examples of which include, accordingly, a coryneform bacterium and a bacterium belonging to the family Enterobacteriaceae. The explanations given hereinafter to the bacterium can be similarly applied to any bacterium that can be used equivalently in the method as described herein.

In a method as described herein, the coryneform bacteria are aerobic gram-positive bacilli, and include *Corynebacterium* bacteria, *Brevibacterium* bacteria, *Microbacterium* bacteria, and so forth. The coryneform bacteria include bacteria which were previously classified into the genus *Brevibacterium*, but have been united into the genus *Corynebacterium* (Liebl W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns, *Int. J. Syst. Bacteriol.*, 1991, 41:255-260). The coryneform bacteria also include bacteria which have previously been classified into *Corynebacterium ammoniagenes*, but are presently reclassified into *Corynebacterium stationis* based upon nucleotide sequence analysis of 16S rRNA and so forth (Bernard K. A. et al., Assignment of *Brevibacterium stationis* (ZoBell and Upham 1944) Breed 1953 to the genus *Corynebacterium*, as *Corynebacterium stationis* comb. nov., and emended description of the genus *Corynebacterium* to include isolates that can alkalinize citrate, *Int. J. Syst. Evol. Microbiol.*, 2010, 60:874-879). One advantage of using the coryneform bacteria is that they are gram-positive bacteria having thick peptidoglycan layer in the bacterial cell wall which makes the bacteria resistant to various environmental conditions such as, for example, temperature and chemically active agents (e.g., oxidative and toxic chemicals). Another advantage of using the coryneform bacteria is that they can grow well in a simple medium containing a saccharide, ammonia, mineral salts, etc., and therefore they are excellent in view of cost of medium, culture method, and culture productivity, and so forth.

Specific examples of coryneform bacteria include the following species:
  *Corynebacterium acetoacidophilum,*
  *Corynebacterium acetoglutamicum,*
  *Corynebacterium alkanolyticum,*
  *Corynebacterium callunae,*
  *Corynebacterium glutamicum,*
  *Corynebacterium lilium,*
  *Corynebacterium melassecola,*
  *Corynebacterium thetmoaminogenes* (*Corynebacterium efficiens*),
  *Corynebacterium herculis,*
  *Brevibacterium divaricatum,*
  *Brevibacterium flavum,*
  *Brevibacterium immariophilum,*
  *Brevibacterium lactofetmentum* (*Corynebacterium glutamicum*),
  *Brevibacterium roseum,*
  *Brevibacterium saccharolyticum,*
  *Brevibacterium thiogenitalis,*
  *Corynebacterium ammonia* genes (*Corynebacterium stationis*),
  *Brevibacterium album,*
  *Brevibacterium cerinum,*
  *Microbacterium ammoniaphilum.*

Specific examples of coryneform bacteria include the following strains:
  *Corynebacterium acetoacidophilum* ATCC 13870,
  *Corynebacterium acetoglutamicum* ATCC 15806,
  *Corynebacterium alkanolyticum* ATCC 21511,
  *Corynebacterium callunae* ATCC 15991,
  *Corynebacterium glutamicum* ATCC 13020, ATCC 13032, ATCC 13060, ATCC 13869, FERM BP-734,
  *Corynebacterium lilium* ATCC 15990,
  *Corynebacterium melassecola* ATCC 17965,
  *Corynebacterium thetmoaminogenes* AJ12340 (FERM BP-1539),
  *Corynebacterium herculis* ATCC 13868,
  *Brevibacterium divaricatum* ATCC 14020,
  *Brevibacterium flavum* ATCC 13826, ATCC 14067, AJ12418 (FERM BP-2205),
  *Brevibacterium immariophilum* ATCC 14068,
  *Brevibacterium lactofetmentum* ATCC 13869,
  *Brevibacterium roseum* ATCC 13825,
  *Brevibacterium saccharolyticum* ATCC 14066,
  *Brevibacterium thiogenitalis* ATCC 19240,
  *Corynebacterium ammoniagenes* (*Corynebacterium stationis*) ATCC 6871, ATCC 6872,
  *Brevibacterium album* ATCC 15111,
  *Brevibacterium cerinum* ATCC 15112,
  *Microbacterium ammoniaphilum* ATCC 15354.

These strains are available from, for example, the American Type Culture Collection (ATCC; Address: P.O. Box 1549, Manassas, Va. 20108, United States of America). That is, registration numbers are assigned to the respective strains, and the strains can be ordered by using these registration numbers (refer to the web site of the ATCC). The registration numbers of the strains are listed in the catalogue of the American Type Culture Collection.

In a method as described herein, the bacteria belonging to the family Enterobacteriaceae can be from the genera *Enterobacter, Erwinia, Escherichia, Klebsiella, Morganella, Pantoea, Photorhabdus, Providencia, Salmonella, Yersinia,* and so forth, and are able to produce glycine. Specifically, those classified into the family Enterobacteriaceae according to the taxonomy used in the NCBI (National Center for Biotechnology Information) database can be used. Examples of strains from the family Enterobacteriaceae which can be modified include a bacterium of the genus *Escherichia*, *Enterobacter* or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *Escherichia coli* K-12, p. 2460-2488. In F. C. Neidhardt et al. (ed.), *Escherichia coli* and *Salmonella*: cellular and molecular biology, $2^{nd}$ ed. ASM Press, Washington, D.C., 1996). The species *Escherichia coli* (*E. coli*) is a particular example. Specific examples of *E. coli* include *E. coli* W3110 (ATCC 27325), *E. coli* MG1655 (ATCC 47076), and so forth, which are derived from the prototype wild-type strain, *E. coli* K-12 strain. These strains are available from, for example, the American Type Culture Collection (ATCC) as explained above.

Examples of the *Enterobacter* bacteria include *Enterobacter agglomerans*, *Enterobacter aerogenes*, and so forth. Examples of the *Pantoea* bacteria include *Pantoea ananatis* (*P. ananatis*), and so forth. Some strains of *Enterobacter agglomerans* were recently reclassified into *Pantoea agglomerans*, *Pantoea ananatis* or *Pantoea stewartii* on the basis of nucleotide sequence analysis of 16S rRNA, etc. A bacterium belonging to either genus *Enterobacter* or *Pantoea* may be used so long as it is a bacterium classified into the family Enterobacteriaceae. When a *P. ananatis* strain is bred by genetic engineering techniques, *P. ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *P. ananatis* on the basis of nucleotide sequencing of 16S rRNA and so forth as described above.

The bacterium as described herein has been modified to overexpress a gene encoding a protein having L-threonine 3-dehydrogenase activity and a gene encoding a protein having 2-amino-3-oxobutanoate coenzyme A ligase activity.

The phrase "a protein having L-threonine 3-dehydrogenase activity" can mean the protein that causes catalysis of the following reaction: L-threonine+NAD$^+$↔L-2-amino-3-oxobutanoate+NADH+2 H$^+$ (Enzyme Commission (EC) number 1.1.1.103; Boylan S. A. and Dekker E. E., L-Threonine dehydrogenase. Purification and properties of the homogeneous enzyme from *E. coli* K-12, *J. Biol. Chem.*, 1981, 256(4):1809-1815). For example, a protein having L-threonine 3-dehydrogenase activity can mean the protein having the amino acid sequence shown in SEQ ID NO: 2 and homologues thereof that can cause catalysis of the reaction of the NAD+-dependent oxidation of L-threonine to L-2-amino-3-oxobutanoate. The activity of a protein having L-threonine 3-dehydrogenase activity can be determined by evaluating colorimetrically the formation of aminoacetone from L-threonine or monitoring the formation of NADH using a spectrophotometer (see Boylan S. A. and Dekker E. E., 1981, and references therein).

The phrase "a protein having 2-amino-3-oxobutanoate coenzyme A ligase activity" can mean the protein that causes catalysis of the following reaction: glycine+acetyl-coenzyme A↔L-2-amino-3-oxobutanoate+coenzyme A+H$^+$ (EC 2.3.1.29; acetyl-coenzyme A is also referred to as Ac-CoA; Mukherjee J. J. and Dekker E. E., Purification, properties, and N-terminal amino acid sequence of homogeneous *E. coli* 2-amino-3-ketobutyrate CoA ligase, a pyridoxal phosphate-dependent enzyme, *J. Biol. Chem.*, 1987, 262:14441-14447). For example, a protein having 2-amino-3-oxobutanoate coenzyme A ligase activity can mean the protein having the amino acid sequence shown in SEQ ID NO: 4 and homologues thereof that can cause catalysis of the reaction of the cleavage of 2-amino-3-oxobutanoate to glycine and acetyl-coenzyme A. The activity a protein having 2-amino-3-oxobutanoate coenzyme A ligase activity can be determined by evaluating colorimetrically the formation of aminoacetone from glycine and Ac-CoA or observing the condensation reaction at 412 nm between coenzyme A (also referred to as CoA) and 5,5'-dithiobis-(2-nitrobenzoic acid) (see, for example, Mukherjee J. J. and Dekker E. E., 1987, and references therein).

The protein concentration can be determined by the Bradford protein assay or the method of Lowry using bovine serum albumin (BSA) as a standard and a Coomassie dye (Bradford M. M., *Anal. Biochem.*, 1976, 72:248-254; Lowry O. H. et al., *J. Biol. Chem.*, 1951, 193:265-275).

An example of the protein having L-threonine 3-dehydrogenase activity can be the protein having the amino acid sequence shown in SEQ ID NO: 2 encoded by the nucleotide sequence shown in SEQ ID NO: 1 which corresponds to the tdh gene. The tdh gene of *E. coli* encodes the L-threonine 3-dehydrogenase TDH, NAD(P)-binding (KEGG, Kyoto Encyclopedia of Genes and Genomes, entry No. b3616; Protein Knowledgebase, UniProtKB/Swiss-Prot, accession No. P07913). The tdh gene (GenBank, accession No. NC_000913.3; nucleotide positions: 3790320 to 3791345, complement; Gene ID: 948139) is located between the kbl gene and the waaH gene on the same strand of the chromosome of *E. coli* strain K-12. The nucleotide sequence of the tdh gene (SEQ ID NO: 1) and the amino acid sequence of the TDH protein (SEQ ID NO: 2) encoded by the tdh gene of *E. coli* are known. Moreover, the amino acid homologues of TDH from different bacterial species are also known such as, for example, the homologues native to the bacteria belonging to the family Enterobacteriaceae, including the species *E. coli* having the TDH of SEQ ID NO: 2 (identity: 100%), *Shigella flexneri* (identity: 99%), *Salmonella* enteric (identity: 98%), *Klebsiella pneumonia* (identity: 97%), *Enterobacter cloacae* (identity: 96%), *P. ananatis* (identity: 86%); the family Burkholderiaceae, including the species *Burkholderia mallei* (identity: 77%), *Paraburkholderia xenovorans* (identity: 76%); the family Rhizobiaceae, including the species *Rhizobium etli* (identity: 71%); the family Xanthomonadaceae, including the species *Xanthomonas axonopodis* (identity: 64%); and so forth (see, for example, the NCBI database, National Center for Biotechnology Information). Therefore, examples of the proteins having L-threonine 3-dehydrogenase activity can also be the proteins that are homologues of the protein having the amino acid sequence shown in SEQ ID NO: 2.

An example of the protein having 2-amino-3-oxobutanoate coenzyme A ligase activity can be the protein having the amino acid sequence shown in SEQ ID NO: 4 encoded by the nucleotide sequence shown in SEQ ID NO: 3 which corresponds to the kbl gene. The kbl gene of *E. coli* encodes the 2-amino-3-oxobutanoate coenzyme A ligase KBL (synonyms: 2-amino-3-ketobutyrate coenzyme A ligase, 2-amino-3-oxobutanoate glycine-lyase (CoA-acetylating), glycine C-acetyltransferase, aminoacetone synthetase, aminoacetone synthase) (KEGG, entry No. b3617; Protein Knowledgebase, UniProtKB/Swiss-Prot, accession No. POAB77). The kbl gene (GenBank, accession No. NC_000913.3; nucleotide positions: 3791355 to 3792551, complement; Gene ID: 948138) is located between the yibB gene and the tdh gene on the same strand of the chromosome of *E. coli* strain K-12. The nucleotide sequence of the kbl gene (SEQ ID NO: 3) and the amino acid sequence of the KBL protein (SEQ ID NO: 4) encoded by the kbl gene of *E. coli* are known. Moreover, the amino acid homologues of KBL from different bacterial species are also known such as, for example, the homologues native to the bacteria belonging to the family Enterobacteriaceae, including the species *E. coli* having the KBL of SEQ ID NO: 4 (identity: 100%), *Shigella dysenteriae* (identity: 99%), *Citrobacter farmer* (identity: 97%), *Salmonella enterica* (identity: 97%), *P. ananatis* (identity: 82%); the family Yersiniaceae, including the species *Serratia marcescens* (identity: 88%); from the family Morganellaceae, including species *Xenorhabdus khoisanae* (identity: 83%); from the family Erwiniaceae, including the species *Erwinia* sp. 9145 (identity: 82%); from the family Xanthomonadaceae, including the species *Lysobacter spongiicola* (identity: 67%), *Stenotrophomonas maltophilia* (identity: 66%); and so forth (see, for example, the NCBI database). Therefore, examples of the proteins having 2-amino-3-oxobutanoate coenzyme A ligase activity can also be the proteins that are homologues of the protein having the amino acid sequence shown in SEQ ID NO: 4.

The phrase "a bacterium modified to overexpress a gene encoding a protein having L-threonine 3-dehydrogenase activity and a gene encoding a protein having 2-amino-3-oxobutanoate coenzyme A ligase activity" can mean that the bacterium has been modified in such a way that in the modified bacterium the total activity of the corresponding gene protein product that causes catalysis of the reaction of the NAD+-dependent oxidation of L-threonine to L-2-amino-3-oxobutanoate and the total activity of the corresponding gene protein product that causes catalysis of the reaction of the cleavage of 2-amino-3-oxobutanoate to glycine and acetyl-coenzyme A are increased, or the expression level of the gene encoding a protein having L-threonine 3-dehydrogenase activity and the expression level of the gene encoding a protein having 2-amino-3-oxobutanoate coenzyme A ligase activity are higher, as compared with those levels in a non-modified strain, for example, a wild-type or parental strain. Examples of a non-modified strain serving as a reference for the above comparison can include a wild-type strain of a coryneform bacterium such as the strain *C. glutamicum* ATCC13032, or a wild-type strain of a bacterium belonging to the family Enterobacteriaceae such as the strains *E. coli* MG1655 (ATCC 47076) and W3110 (ATCC 27325), or a wild-type strain of a bacterium belonging to the genus *Pantoea* such as the strain *P. ananatis* AJ13355 (FERM BP-6614), and so forth.

The bacterium modified to overexpress a gene encoding a protein having L-threonine 3-dehydrogenase activity and a gene encoding a protein having 2-amino-3-oxobutanoate coenzyme A ligase activity can be a bacterium in which the total activity of the corresponding gene protein product that causes catalysis of the reaction of the NAD+-dependent oxidation of L-threonine to L-2-amino-3-oxobutanoate and the total activity of the corresponding gene protein product that causes catalysis of the reaction of the cleavage of 2-amino-3-oxobutanoate to glycine and acetyl-coenzyme A are increased by, for example, introducing and/or increasing the copy number of the gene encoding the protein having L-threonine 3-dehydrogenase activity and the gene encoding the protein having 2-amino-3-oxobutanoate coenzyme A ligase activity, or increasing the activity per molecule (may be referred to as a specific activity) of the proteins encoded by said genes, as compared with a non-modified strain, for example, a wild-type or parental strain. The bacterium may be modified so that the activity of the protein having L-threonine 3-dehydrogenase activity per cell and/or the activity of the protein having 2-amino-3-oxobutanoate coenzyme A ligase activity per cell are/is increased to 150% or more, 200% or more, 300% or more, of the activity of that protein(s) in a non-modified strain. It is preferred that the bacterium is modified in such a way that in the modified bacterium, the activity of the protein having L-threonine 3-dehydrogenase activity per cell and the activity of the protein having 2-amino-3-oxobutanoate coenzyme A ligase activity per cell are increased as compared with those activities in a non-modified strain.

The phrase "a bacterium modified to overexpress a gene encoding a protein having L-threonine 3-dehydrogenase activity and a gene encoding a protein having 2-amino-3-oxobutanoate coenzyme A ligase activity" can also be applied to a bacterium in which the expression level of a gene encoding a protein having L-threonine 3-dehydrogenase activity and the expression level of a gene encoding a protein having 2-amino-3-oxobutanoate coenzyme A ligase activity are enhanced as compared with a non-modified strain, for example, a wild-type or parental strain. Therefore, the phrase "a bacterium modified to overexpress a gene encoding a protein having L-threonine 3-dehydrogenase activity and a gene encoding a protein having 2-amino-3-oxobutanoate coenzyme A ligase activity" can also mean that the expression level of a gene encoding a protein having L-threonine 3-dehydrogenase activity and/or the expression level of a gene encoding a protein having 2-amino-3-oxobutanoate coenzyme A ligase activity are/is higher than that level(s) in a non-modified strain. It is preferred that the bacterium is modified in such a way that in the modified bacterium the expression level of a gene encoding a protein having L-threonine 3-dehydrogenase activity and the expression level of a gene encoding a protein having 2-amino-3-oxobutanoate coenzyme A ligase activity are higher as compared with those levels in a non-modified strain.

Methods for modifying a bacterium to overexpress a gene encoding a protein having L-threonine 3-dehydrogenase activity and a gene encoding a protein having 2-amino-3-oxobutanoate coenzyme A ligase activity, and methods which can be used to enhance expression of the gene encoding a protein having L-threonine 3-dehydrogenase activity and the gene encoding a protein having 2-amino-3-oxobutanoate coenzyme A ligase activity in the bacterium as described herein may depend on the bacterium that is chosen for the modification. Any method for gene overexpression may be used so long as the overexpression of the gene can be attained using that method. Therefore, the gene encoding a protein having L-threonine 3-dehydrogenase activity and the gene encoding a protein having 2-amino-3-oxobutanoate coenzyme A ligase activity can be overexpressed using one method for gene overexpression, or the genes can be overexpressed using different methods for gene overexpression.

The bacterium as described herein can be modified to overexpress a gene encoding a protein having L-threonine 3-dehydrogenase activity and a gene encoding a protein having 2-amino-3-oxobutanoate coenzyme A ligase activity so that the bacterium can harbor said genes after introducing the genes. Also, the bacterium can be modified in such a way that the activity of the protein having L-threonine 3-dehydrogenase activity and the activity of the protein having 2-amino-3-oxobutanoate coenzyme A ligase activity can be determined in the modified bacterium. That is, any bacterium natively or naturally not having a gene encoding a protein having L-threonine 3-dehydrogenase activity and a gene encoding a protein having 2-amino-3-oxobutanoate coenzyme A ligase activity can be used so long as the bacterium can be modified to overexpress the gene encoding a protein having L-threonine 3-dehydrogenase activity and the gene encoding a protein having 2-amino-3-oxobutanoate coenzyme A ligase activity so that the activity of the protein having L-threonine 3-dehydrogenase activity and the activity of the protein having the activity of 2-amino-3-oxobutanoate coenzyme A ligase can be determined in the modified bacterium and the modified bacterium is able to produce glycine as described herein.

The bacterium as described herein can be obtained by introducing a gene encoding a protein having L-threonine 3-dehydrogenase activity and a gene encoding a protein having 2-amino-3-oxobutanoate coenzyme A ligase activity into the bacterium, which does not have said genes before the introduction of the genes, so that the bacterium harbors the gene encoding a protein having L-threonine 3-dehydrogenase activity and the gene encoding a protein having 2-amino-3-oxobutanoate coenzyme A ligase activity. The phrase "a bacterium modified to harbor a gene encoding a protein having L-threonine 3-dehydrogenase activity and a gene encoding a protein having 2-amino-3-oxobutanoate coenzyme A ligase activity" can mean that the bacterium belonging to the first bacterial species, naturally or natively not having the gene encoding a protein having L-threonine 3-dehydrogenase activity and the gene encoding a protein having 2-amino-3-oxobutanoate coenzyme A ligase activity and thus referred to as a "recipient bacterium" (so-called a host organism), has been modified to harbor the gene encoding a protein having L-threonine 3-dehydrogenase activity and the gene encoding a protein having 2-amino-3-oxobutanoate coenzyme A ligase activity native to the second bacterial species which is different from the first species (so-called a donor bacterium). The donor bacterium may be a bacterium of one species, or it may be a bacterium of two different species, provided that it is not the recipient bacterium. Therefore, a gene encoding a protein having L-threonine 3-dehydrogenase activity and a gene encoding a protein having 2-amino-3-oxobutanoate coenzyme A ligase activity may be native to a bacterium of one species or two different species. Examples of the recipient bacterium include a coryneform bacterium as described herein, including a bacterium belonging to the genus *Corynebacterium* or *Brevibacterium*. Examples of the donor bacterium include bacteria belonging to the family Enterobacteriaceae as described herein, including bacteria belonging to the genus *Escherichia* and *Pantoea*. For example, when the gene encoding a protein having L-threonine 3-dehydrogenase activity and the gene encoding a protein having 2-amino-3-oxobutanoate coenzyme A ligase activity are native to a bacterium of one species, the recipient bacterium may be a coryneform bacterium such as, for example, a bacterium of the species *C. glutamicum*, and the donor bacterium may be a bacterium of the species *E. coli*.

The bacterium as described herein has been modified to harbor a gene encoding a protein having L-threonine 3-dehydrogenase activity and a gene encoding a protein having 2-amino-3-ketobutyrate CoA ligase activity. The gene encoding a protein having L-threonine 3-dehydrogenase activity and the gene encoding a protein having 2-amino-3-ketobutyrate CoA ligase activity can be overexpressed in the bacterium in such a way that the genes are present on different nucleic acid molecules. Alternatively, the genes can be introduced into the bacterium in such a way that the genes are present on one nucleic acid molecule. For example, the gene encoding a protein having L-threonine 3-dehydrogenase activity and the gene encoding a protein having an activity of 2-amino-3-ketobutyrate CoA ligase may be present on one expression vector or on the chromosome. Alternatively, the genes may be present on two different expression vectors. Alternatively, a gene may be present on one expression vector and another gene may be present on the chromosome.

A coryneform bacterium serving as a recipient bacterium can be an example of the bacterium as described herein, and the methods for overexpression of a gene encoding a protein having L-threonine 3-dehydrogenase activity and a gene encoding a protein having 2-amino-3-oxobutanoate coenzyme A ligase activity in a coryneform bacterium are described hereinafter.

A method for the overexpression of a gene encoding a protein having L-threonine 3-dehydrogenase activity and a gene encoding a protein having 2-amino-3-oxobutanoate coenzyme A ligase activity in a coryneform bacterium can be introducing a nucleic acid (DNA) having the gene(s) into the coryneform bacterium. Methods which can be used to introduce a nucleic acid such as, for example, a gene, a vector, and the like into a coryneform bacterium can include, but are not limited to, genetic engineering methods known to the person of ordinary skill in the art, and these are not particularly limited. In the bacterium as described herein, the gene encoding a protein having L-threonine 3-dehydrogenase activity and the gene encoding a protein having 2-amino-3-oxobutanoate coenzyme A ligase activity can be present on a vector that autonomously replicates outside of the chromosome, such as a plasmid, or may be incorporated into the chromosome. In addition, as described above, to construct the bacterium as described herein, introduction of the gene encoding a protein having L-threonine 3-dehydrogenase activity and the gene encoding a protein having 2-amino-3-oxobutanoate coenzyme A ligase activity and impartation or enhancement of the ability to produce glycine can be performed in an arbitrary order.

A nucleic acid can be introduced into a coryneform bacterium by using, for example, a vector. The vector is not particularly limited so long as a vector autonomously replicable in a coryneform bacterium is chosen, and may be, for example, a vector native to a bacterial plasmid, a vector native to a yeast plasmid, a vector native to a bacteriophage, cosmid, phagemid, or the like. As the vector, for example, a plasmid native to a coryneform bacterium can be used. Also, as the vector, a vector autonomously replicable in a cell of the coryneform bacterium can be used. The vector can be a multi-copy vector. Furthermore, the vector can include a marker such as an antibiotic resistance gene for selection of transformants. The vector may be, for example, a vector native to a bacterial plasmid, a vector native to a yeast plasmid, a vector native to a bacteriophage, cosmid, phagemid, or the like. Specific examples of vector autonomously replicable in coryneform bacteria can include pHM1519 (Miwa K. et al., *Agric. Biol. Chem.*, 1984, 48:2901-2903); pAM330 (Miwa K. et al., 1984); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAM330 described in Japanese Patent Laid-open (Kokai) No. 58-67679; pHM1519 described in Japanese Patent Laid-open (Kokai) No. 58-77895; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVC7 described in Japanese Patent Laid-open (Kokai) No. 9-070291; and so forth.

Furthermore, an artificial transposon and so forth can also be used to introduce a nucleic acid into a coryneform bacterium. When a transposon is used, a protein-encoding gene can be introduced into a chromosome by homologous recombination or translocation ability of the transposon itself. Other examples of the introduction method utilizing homologous recombination can include, for example, the methods utilizing a linear DNA, a plasmid having a temperature sensitive replication origin, a plasmid capable of conjugative transfer, a suicide vector not having a replication origin that does not function in the chosen host, and so forth. A gene to be introduced into a coryneform bacterium may be used as it is, or it may be modified so that it has the optimal codons according to codon frequencies in the coryneform bacterium. Specifically, the expression of a gene, which is native to a donor bacterium, in a recipient bacterium can be achieved by substituting rare (low-usage in the host organism) codons in the gene for synonymous middle- or high-usage codons, where codon usage can be defined as the number of times (frequency) a codon is translated per unit time in the cell of an organism or an average codon frequency of the sequenced protein-coding reading frames of an organism (Zhang S. P. et al., *Gene*, 1991, 105(1):61-72). The codon usage per organism can be found in the Codon Usage Database, which is an extended web-version of the CUTG (Codon Usage Tabulated from GenBank) (kazusa.or.jp/codon; Nakamura Y. et al., Codon usage tabulated from the international DNA sequence databases: status for the year 2000, *Nucleic Acids Res.*, 2000, 28(1):292). The substitution of low-usage codons for synonymous high-usage codons can be preferable. The substituting rare and/or low-usage codons for synonymous middle- or high-usage codons may be combined with co-expression of the genes which encode tRNAs recognizing rare codons.

A gene to be introduced into the bacterium as described herein can be ligated downstream from the promoter sequence. The promoter is not particularly limited so long as one that functions in a coryneform bacterium is chosen, and it may be a promoter native to a coryneform bacterium, or it may be a heterologous promoter. The "promoter that functions in a coryneform bacterium" can refer to a promoter that possesses promoter activity in a coryneform bacterium. Specific examples of the heterologous promoter include, for example, promoters native to *E. coli* such as tac promoter, lac promoter, trp promoter, and araBAD promoter. Among these, potent promoters such as the tac promoter are particular examples, and inducible promoters such as the araBAD promoter are also particular examples.

As the promoter, an existing promoter that is highly active may be obtained by using various reporter genes. For example, by making the −35 and −10 regions in a promoter region closer to a consensus sequence, the activity of the promoter can be enhanced (WO0018935 A1). Examples of the method for evaluating strength of a promoter and strong promoters are described in the paper of Goldstein M. A. et al. (Prokaryotic promoters in biotechnology, *Biotechnol. Annu. Rev.*, 1995, 1:105-128) and so forth. Furthermore, it is known that substitution, insertion, or deletion of several nucleotides in a spacer region between the ribosome-binding site (RBS) and the start codon, especially in a sequence immediately upstream of the start codon (5'-UTR), significantly affects stability and translation efficiency of mRNA, and these sequences can also be modified.

The method for introducing a gene into a coryneform bacterium is not particularly limited, and typical method, for example, the protoplast method (Miwa K. et al., *Gene*, 1985, 39:281-286), the electroporation method (Dunican L. K. and Shivnan E., *Nat. Biotechnol.*, 1989, 7:1067-1070), the electric pulse method (JP H2-207791 A), and so forth can be used.

As a bacterium belonging to the family Enterobacteriaceae can be an example of the bacterium as described herein, the methods for overexpression of a gene encoding a protein having L-threonine 3-dehydrogenase activity and a gene encoding a protein having 2-amino-3-oxobutanoate coenzyme A ligase activity in a bacterium belonging to the family Enterobacteriaceae are described hereinafter.

Methods which can be used to enhance expression of a gene include, but are not limited to, increasing a gene copy number in the bacterial genome (in the chromosome and/or in the autonomously replicating plasmid) and/or introducing a gene encoding a protein having the desired activity into a vector that is able to increase the copy number and/or the expression level of the gene in the bacterium as described herein according to genetic engineering methods known to those of ordinary skill in the art.

Examples of the vectors can include, but are not limited to, broad-host-range plasmids such as pMW118/119, pBR322, pUC19, and the like. Multiple copies of a gene encoding a protein having L-threonine 3-dehydrogenase activity and/or a gene encoding a protein having 2-amino-3-ketobutyrate CoA ligase activity can also be introduced into the chromosomal DNA of a bacterium by, for example, homologous recombination, Mu-driven integration, or the like. Homologous recombination can be carried out using a sequence in which multiple copies exist in the chromosomal DNA as a target. Sequences with multiple copies in the chromosomal DNA can include, but are not limited to, repetitive DNA or inverted repeats present at the end of a transposable element. In addition, it is possible to incorporate a gene into a transposon and allow it to be transferred to introduce multiple copies of the gene into the chromosomal DNA. By using Mu-driven integration, more than 3 copies of the gene can be introduced into the chromosomal DNA during a single act (Akhverdyan V. Z. et al., *Biotechnol. (Russian)*, 2007, 3:3-20).

The other methods which can be used to enhance expression of a gene encoding a protein having L-threonine 3-dehydrogenase activity and a gene encoding a protein having 2-amino-3-oxobutanoate coenzyme A ligase activity include increasing the expression level of the genes by modification of adjacent regulatory region(s) of that genes or introducing native and/or modified foreign regulatory region(s). As the gene encoding a protein having L-threonine 3-dehydrogenase activity and/or the gene encoding a protein having 2-amino-3-oxobutanoate coenzyme A ligase activity encoding may be organized in operon structure, the method which can be used to enhance expression of the genes also includes increasing the expression level of the operon having that gene(s) by modification of adjacent regulatory region(s) of the operon or introducing native and/or modified foreign regulatory region(s). In this method, the expression of one or more genes, including the gene encoding a protein having L-threonine 3-dehydrogenase activity and the gene encoding a protein having 2-amino-3-oxobutanoate coenzyme A ligase activity, can be enhanced at the same time.

Expression regulatory regions or sequences can be exemplified by promoters, enhancers, attenuators and termination signals, anti-termination signals, ribosome-binding sites (RBS) and other expression control elements (e.g., regions to which repressors or inducers bind and/or binding sites for transcriptional and translational regulatory proteins, for example, in the transcribed mRNA). Such regulatory regions are described, for example, in Sambrook J., Fritsch E. F. and Maniatis T., "Molecular Cloning: A Laboratory Manual", $2^{nd}$ ed., Cold Spring Harbor Laboratory Press (1989). Modifications of regions controlling gene(s) expression can be combined with increasing the copy number of the modified gene(s) in bacterial genome using known methods (see, for example, Akhverdyan V. Z. et al., *Appl. Microbiol. Biotechnol.*, 2011, 91:857-871; Tyo K. E. J. et al., *Nature Biotechnol.*, 2009, 27:760-765).

The exemplary promoters suitable for enhancing expression of a gene encoding a protein having L-threonine 3-dehydrogenase activity and a gene encoding a protein having 2-amino-3-ketobutyrate CoA ligase activity can be the potent promoters that are stronger than the native promoters of those genes. For example, the lac promoter, the tip promoter, the trc promoter, the tac promoter, the PR or the $P_L$ promoters of lambda phage are all known to be potent promoters. Potent promoters providing a high level of gene expression in a bacterium belonging to the family Enterobacteriaceae can be used. Alternatively, the effect of a promoter can be enhanced by, for example, introducing a mutation into the promoter region of a gene to obtain a stronger promoter function, thus resulting in the increased transcription level of the gene located downstream from the promoter. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629).

The copy number, presence or absence of the gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the persons of ordinary skill in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

Any methods for manipulation with recombinant DNA can be used including conventional methods such as, for example, transformation, transfection, infection, conjugation, and mobilization. Transformation, transfection, infection, conjugation or mobilization of a bacterium with the DNA encoding a protein can impart to the bacterium the ability to synthesize the protein encoded by the DNA. Methods of transformation, transfection, infection, conjugation, and mobilization include any known methods. For example, a method of treating recipient cells with calcium chloride so as to increase permeability of the cells of *E. coli* K-12 to DNA has been reported for efficient DNA transformation and transfection (Mandel M. and Higa A., Calcium-dependent bacteriophage DNA infection, *J. Mol. Biol.*, 1970, 53:159-162). Methods of specialized and/or generalized transduction were described (Morse M. L. et al., Transduction in *Escherichia coli* K-12, Genetics, 1956, 41(1):142-156; Miller J. H., *Experiments in Molecular Genetics*. Cold Spring Harbor, N.Y.: Cold Spring Harbor La. Press, 1972). Other methods for random and/or targeted integration of DNA into the host microorganism can be applied, for example, "Mu-driven integration/amplification" (Akhverdyan et al., *Appl. Microbiol. Biotechnol.*, 2011, 91:857-871), "Red/ET-driven integration" or "λRed/ET-mediated integration" (Datsenko K. A. and Wanner B. L., *Proc. Natl. Acad. Sci. USA* 2000, 97(12):6640-45; Zhang Y., et al., *Nature Genet.*, 1998, 20:123-128). Moreover, for multiple insertions of desired genes in addition to Mu-driven replicative transposition (Akhverdyan et al., *Appl. Microbiol. Biotechnol.*, 2011, 91:857-871) and chemically inducible chromosomal evolution based on recA-dependent homologous recombination resulted in amplification of desired genes (Tyo K. E. J. et al., *Nature Biotechnol.*, 2009, 27:760-765), another methods can be used, which utilize different combinations of transposition, site-specific and/or homologous Red/ET-mediated recombinations, and/or P1-mediated generalized transduction (see, for example, Minaeva N. et al., *BMC Biotechnology*, 2008, 8:63; Koma D. et al., *Appl. Microbiol. Biotechnol.*, 2012, 93(2):815-829).

Methods for overexpression of a gene encoding a protein having L-threonine 3-dehydrogenase activity and a gene encoding a protein having 2-amino-3-ketobutyrate CoA ligase activity in bacterial species other than a coryneform bacterium and a bacterium belonging to the family Enterobacteriaceae can be similarly applied by referring to the methods described herein for the coryneform bacterium and the bacterium belonging to the family Enterobacteriaceae, or those methods can be used that are known to the persons of ordinary skill in the art. Furthermore, it is within the ordinary skill that common methods can be used that are suitable for the gene overexpression in a coryneform bacterium and a bacterium belonging to the family Enterobacteriaceae. Moreover, the methods suitable for the gene overexpression in a coryneform bacterium can be appropriately modified and used to overexpress a gene in a bacterium belonging to the family Enterobacteriaceae, and contrariwise. Therefore, the methods for gene overexpression as described herein may, virtually, be applied to any bacterium as described herein.

The below descriptions of variants of the gene native to a bacterium of the species *E. coli* and encoding the protein having L-threonine 3-dehydrogenase activity can also be similarly applied to any gene and protein encoded by that gene, including a gene native to the bacterial species other than *E. coli* and encoding a protein having L-threonine 3-dehydrogenase activity, and a gene native to different bacterial species and encoding a protein having 2-amino-3-ketobutyrate CoA ligase activity.

There may be differences in DNA sequences between the bacterial families, genera, species, or strains. Therefore, the gene encoding a protein having L-threonine 3-dehydrogenase activity is not limited to the gene shown in SEQ ID NO: 1, but also may include genes which are variant nucleotide sequences of or homologous to SEQ ID NO: 1 and encode variants of the protein having L-threonine 3-dehydrogenase activity.

The phrase "a variant protein" can mean a protein which has one or more mutations in the sequence as compared with the amino acid sequence shown in SEQ ID NO: 2, whether they are substitutions, deletions, insertions, and/or additions of one or several amino acid residues, but still maintains the L-threonine 3-dehydrogenase activity as described herein, or the three-dimensional structure of the protein is not significantly changed relative to the non-modified protein such as, for example, the wild-type protein TDH having the amino acid sequence shown in SEQ ID NO: 2. The number of changes in the variant protein depends on the position of amino acid residue(s) in the three-dimensional structure of the protein or the type of amino acid residue(s). It can be, but is not strictly limited to, 1 to 50, in another example 1 to 30, in another example 1 to 15, in another example 1 to 10, and in another example 1 to 5, in SEQ ID NO: 2. This is possible because amino acids can have high homology to one another so that the activity cannot be affected by such a change, or the three-dimensional structure of the protein cannot be significantly changed relative to the non-modified protein such as, for example, the wild-type protein. Therefore, the protein variants encoded by variant nucleotide sequences of the gene encoding the protein having L-threonine 3-dehydrogenase activity may have a homology, defined as the parameter "identity" when using the computer program BLAST, of not less than 60%, not less than 70%, not less than 75%, not less than 80%, not less than 85%, not less than 90%, not less than 95%, not less than 98%, or not less than 99% with respect to the entire amino acid sequence shown in SEQ ID NO: 2 as long as the L-threonine 3-dehydrogenase activity of the protein is maintained, or the three-dimensional structure of the protein is not significantly changed relative to the non-modified protein such as, for example, the wild-type protein.

The exemplary substitution, deletion, insertion, and/or addition of one or several amino acid residues can be a conservative mutation(s). The representative conservative mutation can be a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution Asn, Glu or Gln for Asp, substitution of Ser or Ala for Cys, substitution Asn, Glu, Lys, His, Asp or Arg for Gln, substitution Asn, Gln, Lys or Asp for Glu, substitution of Pro for Gly, substitution Asn, Lys, Gln, Arg or Tyr for His, substitution of Leu, Met, Val or Phe for Ile, substitution of Ile, Met, Val or Phe for Leu, substitution Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutation(s) in the different position(s) of amino acids sequence so that the L-threonine 3-dehydrogenase activity of the variant protein is maintained, or the three-dimensional structure of the protein is not significantly changed relative to the non-modified protein such as, for example, the wild-type protein.

To evaluate the degree of protein or DNA homology, several calculation methods can be used, such as a BLAST search, FASTA search and ClustalW method. The BLAST (Basic Local Alignment Search Tool search is the heuristic search algorithm employed by the programs blastp, blastn, blastx, megablast, tblastn, and tblastx; these programs ascribe significance to their findings using the statistical methods of Karlin S. and Altschul S. F. ("Methods for assessing the statistical significance of molecular sequence features by using general scoring schemes" *Proc. Natl. Acad. Sci. USA,* 1990, 87:2264-2268; "Applications and statistics for multiple high-scoring segments in molecular sequences". *Proc. Natl. Acad. Sci. USA,* 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.,* 1990, 183:63-98). The ClustalW method is described by Thompson J. D. et al. ("CLUSTAL W: improving the sensitivity of progressive multiple sequence alignment through sequence weighting, position-specific gap penalties and weight matrix choice", *Nucleic Acids Res.,* 1994, 22:4673-4680).

Moreover, a gene encoding a protein having L-threonine 3-dehydrogenase activity can be a variant nucleotide sequence. The phrase "a variant nucleotide sequence" can mean the nucleotide sequence which encodes a variant protein using any synonymous amino acid codons according to the standard genetic code table (see, e.g., Lewin B., "Genes VIII", 2004, Pearson Education, Inc., Upper Saddle River, N.J. 07458). Therefore, the gene encoding a protein having L-threonine 3-dehydrogenase activity can be a variant nucleotide sequence due to the degeneracy of the genetic code.

The phrase "a variant nucleotide sequence" can also mean, but is not limited to, a nucleotide sequence that is able to hybridize under stringent conditions with the nucleotide sequence complementary to the sequence shown in SEQ ID NO: 1 or a probe that can be prepared from the nucleotide sequence under stringent conditions provided that it encodes a protein having L-threonine 3-dehydrogenase activity. "Stringent conditions" can include those conditions under which a specific hybrid, for example, a hybrid having homology, defined as the parameter "identity" when using the computer program BLAST, of not less than 60%, not less than 70%, not less than 75%, not less than 80%, not less than 85%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate) at 60° C., 0.1×SSC, 0.1% SDS at 60° C., or 0.1×SSC, 0.1% SDS at 65° C. Duration of washing can depend on the type of membrane used for the blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1 may also be used. Such a probe can be produced by PCR (polymerase chain reaction; refer to White T. J. et al., The polymerase chain reaction, *Trends Genet.*, 1989, 5:185-189) using oligonucleotides as primers prepared on the basis of the sequence shown in SEQ ID NO: 1 and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after the hybridization can be, for example, 2×SSC, 0.1% SDS at 50° C., 60° C. or 65° C.

As the gene encoding a protein having L-threonine 3-dehydrogenase activity and native to the species *E. coli* has already been elucidated (see above), the genes native to other bacterial species of the family Enterobacteriaceae and encoding the proteins having L-threonine 3-dehydrogenase activity, and the variant nucleotide sequences encoding variant proteins of the protein having L-threonine 3-dehydrogenase activity can be obtained by PCR utilizing a bacterium of the family Enterobacteriaceae and oligonucleotide primers prepared based on the nucleotide sequence of the tdh gene native to the bacterium; or the site-directed mutagenesis method by treating a DNA containing the wild-type tdh gene, in vitro, for example, with hydroxylamine, or a method for treating a microorganism, for example, a bacterium belonging to the family Enterobacteriaceae harboring the wild-type tdh gene with ultraviolet (UV) irradiation or a mutating agent such as N-methyl-N'-nitro-N-nitrosoguanidine (NTG) and nitrous acid usually used for the such treatment; or chemically synthesized as full-length gene structure. Genes encoding the proteins having L-threonine 3-dehydrogenase activity or variant proteins thereof from other bacterial species can be obtained in a similar manner.

The phrase "wild-type", which can be equivalent to the phrases "native" and "natural", as used herein as to a gene (for example, "a wild-type gene") and a protein (for example, "a wild-type protein") can mean, respectively, a native gene and a native protein that exist, and/or is expressed naturally in, and/or produced by a wild-type bacterium, for example, a wild-type strain of a coryneform bacterium such as, for example, the *C. glutamicum* ATCC13032 strain, or a bacterium of the family Enterobacteriaceae such as, for example, the *E. coli* MG1655 strain (ATCC 47076), the *E. coli* W3110 strain (ATCC 27325), the *P. ananatis* AJ13355 strain (FERM BP-6614), and so forth. As a protein is encoded by a gene, "a wild-type protein" can be encoded by "a wild-type gene" naturally occurring in genome of a wild-type bacterium.

The phrase "native to" in reference to a protein or a nucleic acid native to a particular species such as, for example, a bacterial species can refer to a protein or a nucleic acid that is native to that species. That is, a protein or a nucleic acid native to a particular species can mean the protein or the nucleic acid, respectively, that exists naturally in the species and can be isolated from that species and sequenced using means known to the one of ordinary skill in the art. Moreover, as the amino acid sequence or the nucleotide sequence of a protein or nucleic acid, respectively, isolated from a species in which the protein or nucleic acid exists, can easy be determined, the phrase "native to" in reference to a protein or a nucleic acid can also refer to a protein or a nucleic acid that can be obtained using, for example, a genetic engineering technique, including recombinant DNA technology, or a chemical synthesis method, or the like, so long as the amino acid sequence of the protein or the nucleotide sequence of the nucleic acid thus obtained is identical, accordingly, to the amino acid sequence of the protein or the nucleotide sequence of the nucleic acid that exists naturally in the species. Examples of amino acid sequences native to particular species include, but are not limited to, peptides, oligopeptides, polypeptides, including proteins, specifically enzymes, and so forth. Examples of nucleotide sequences native to particular species include deoxyribonucleic acid (DNA) and ribonucleic acid (RNA), and these are not limited to regulatory sequences, including promoters, attenuators, terminators, and the like, genes, intergenic sequences, sequences encoding signal peptides, pro-moieties of proteins, artificial amino acid sequences, and so forth. Specific examples of amino acid sequences and nucleotide sequences, and homologues thereof native to various species are described herein, and these examples include TDH and KBL having the amino acid sequences shown in SEQ ID NOs: 2 and 4, respectively, which are native to the bacterium of the species *E. coli*, encoded by the corresponding genes having the nucleotide sequences shown in SEQ ID NOs: 1 and 3.

The bacterium can have, in addition to the properties already mentioned, other specific properties such as various nutrient requirements, drug resistance, drug sensitivity, and drug dependence.

2. Method

A method of producing glycine or a salt thereof using a bacterium as described herein includes the steps of cultivating (also called culturing) the bacterium in a culture medium to allow glycine or a salt thereof to be produced, excreted or secreted, and/or accumulated in the culture medium or in the bacterial cells, or both, and collecting glycine or a salt thereof from the culture medium and/or the bacterial cells. The method may include, optionally, the step of purifying glycine or a salt thereof from the culture medium and/or the bacterial cells. Glycine can be produced in a free form or as a salt thereof, or as a mixture of them. For example, sodium, potassium, ammonium, and the like salts or an inner salt such as zwitterion of glycine can be produced by the method. This is possible as amino acids can react under fermentation conditions with each other or a neutralizing agent such as an inorganic or organic acidic or alkaline substance in a typical acid-base neutralization reaction to form a salt that is the chemical feature of amino acids which is apparent to persons of ordinary skill in the art.

The cultivation of the bacterium, and collection and purification of glycine or a salt thereof from the medium and the like may be performed in a manner similar to the conventional fermentation methods wherein glycine or a salt thereof is produced using a microorganism. The culture medium can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolyzates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as from soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, vitamin B12, required substances, for example, organic nutrients such as nucleic acids such as adenine and RNA, amino acids, peptone, casamino acid, yeast extract, and the like may be present in appropriate, even if trace, amounts. Other than these, small amounts of calcium phosphate, iron ions, manganese ions, and so forth may be added, if necessary.

Cultivation can be performed under the conditions suitable for cultivating a bacterium chosen for the use in the method for producing glycine or a salt thereof. For example, when a coryneform bacterium is cultivated, the cultivation can be performed under aerobic conditions for from 24 to 96 hours, the temperature can be maintained at from 24° C. to 42° C., and the pH can be maintained at from 5 to 9. When a bacterium belonging to the family Enterobacteriaceae such as, for example, a bacterium belonging to the genus *Escherichia* is cultivated, the cultivation can be performed under aerobic conditions for from 16 to 72 hours or for from 32 to 48 hours, the culture temperature during cultivation can be controlled within from 30 to 45° C. or within from 30 to 37° C., and the pH can be adjusted between 5 and 8 or between 6 and 7.5. The pH can be adjusted using an inorganic or organic acidic or alkaline substance such as urea, calcium carbonate or ammonia gas.

After cultivation, the cells can be disrupted using methods that are well-known in the art, for example, ultrasonic lysis using high frequency sound waves, or the like, and glycine or a salt thereof can be collected from the supernatant obtained by removing solids such as the cells and the cell-disrupted suspension (so-called cell debris) by centrifugation or membrane filtration, and then the target glycine or a salt thereof can be recovered from the fermentation liquor using conventional techniques such as, for example, concentration, crystallization, ion-exchange chromatography, medium or high pressure liquid chromatography, or a combination of these.

EXAMPLES

The present invention is more precisely explained below with reference to the following non-limiting Examples.

Example 1. Production of Glycine Using a *C. glutamicum* Strain Cultivated in a Medium Supplemented with L-Threonine 1.1 Design and Chemical Synthesis of DNA Fragments <KBL> and <TDH>.

The structure of DNA fragments <KBL> and <TDH> that were used to construct the *C. glutamicum* strain is shown in FIG. 1. The DNA fragments contained a promoter as the regulatory part of the genes kbl and tdh, and a structural part of that genes. The DNA-fragments were synthesized chemically (ATG Service Gene; Russian Federation, St. Petersburg).

The DNA fragment <KBL> having the nucleotide sequence shown in SEQ ID NO: 5 includes:

i) a promoter of the rplK gene (shown as $P_{rplK}$ in FIG. 1A). The nucleotide sequence of the promoter $P_{rplK}$ corresponds to the nucleotides from 638849 to 639029 in the complete genome sequence of the *C. glutamicum* R strain (GenBank, accession No. AP009044.1), and ii) a structural part of the kbl gene having the nucleotide sequence shown in SEQ ID NO: 3 native to *E. coli* strain K-12 substr. MG1655.

Figure 1B:
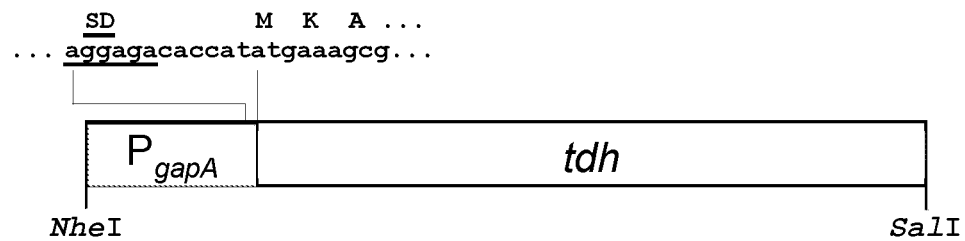

The DNA fragment <TDH> having the nucleotide sequence shown in SEQ ID NO: 6 includes:

i) a promoter of the gapA gene (shown as $P_{gapA}$ in FIG. 1B). The nucleotide sequence of the promoter $P_{gapA}$ corresponds to the nucleotides from 1822219 to 1821813 in the complete genome sequence of the *C. glutamicum* R strain (see above), and ii) a structural part of the tdh gene having the nucleotide sequence shown in SEQ ID NO: 1 native to *E. coli* strain K-12 substr. MG1655.

1.2. Construction of *C. glutamicum* ATCC13032/pPK4 and ATCC13032/pPK4-kbl-tdh strains.

Figure 2:
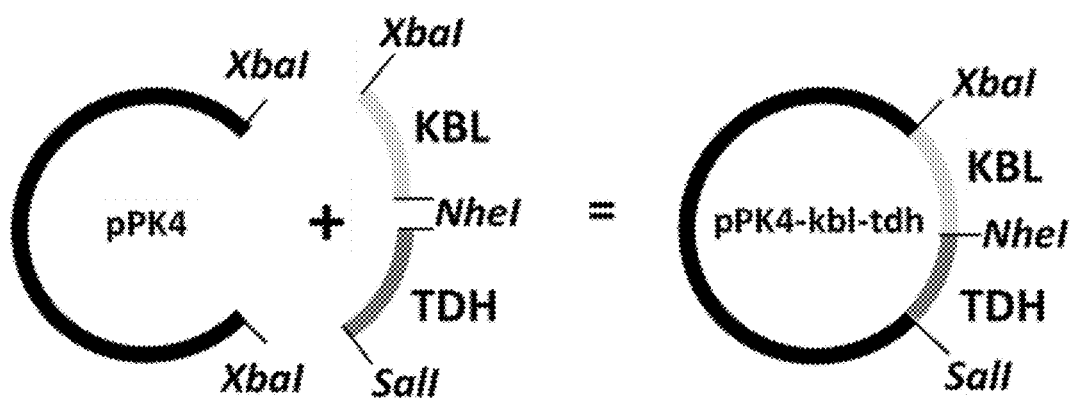
FIG. 2 shows the scheme for construction of pPK4-kbl-tdh plasmid.
Figure 3:
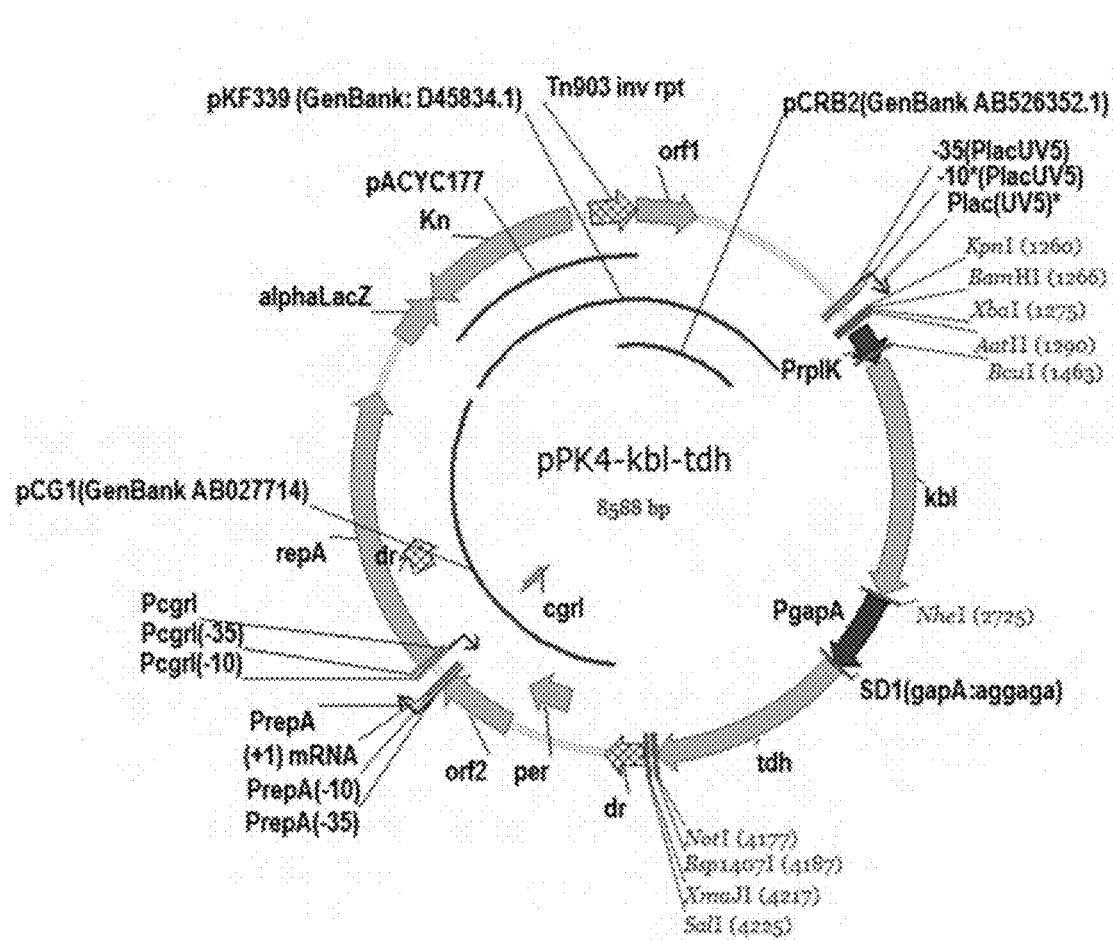
FIG. 3 shows the physical map of pPK4-kbl-tdh plasmid.

The scheme for construction of the pPK4-kbl-tdh plasmid is shown in FIG. 2. All enzymes and protocols were obtained from Fermentas (Thermo Fisher Scientific). To construct the pPK4-kbl-tdh plasmid, the DNA fragments <KBL> and <TDH> were each digested using restrictases NheI and XbaI or SalI and ligated using T4 DNA ligase with the *C. glutamicum/E. coli* shuttle vector pPK4 (U.S. Pat. No. 6,090,597 A) digested using restrictases XbaI and NheI. The *E. coli* JM109 strain (Promega, cat. No. P9751) was transformed by the mixture obtained after the ligation. The obtained pPK4-kbl-tdh plasmid (FIG. 3) was screened among plasmids isolated from 5-20 arbitrary chosen kanamycin-resistant ($Kn^R$) colonies. The structure of the plasmids was verified using restriction analysis and sequencing. As a result, the *C. glutamicum* ATCC13032/pPK4-kbl-tdh strain was constructed. As a control strain, the *C. glutamicum* ATCC13032/pPK4 strain harboring the vector pPK4 was constructed using the same procedure.

1.3. Cultivation of *C. glutamicum* ATCC13032/pPK4 and ATCC13032/pPK4-Kbl-Tdh Strains.

1.3.1. Culture Medium MM*.

The following stock solutions were used:
A—Thiamine hydrochloride, solution in water, 1.6 g/L;
B—Biotin, solution in water, 1 g/L;
C—D,L-Methionine, solution in water, 15 g/L;
D—Glucose, solution in 1 N HCl, 40% (w/v), sterile;
E—MgSO$_4$, solution in water, 1 M;
F—Kanamycin, solution in water (100 g/L).
Component 1 was prepared using:
($NH_4)_2SO_4$—3 g;
$KH_2PO_4$—0.3 g;
Yeast extract—0.2 g;

FeSO$_4$x7H$_2$O—30 mg;
MnSO$_4$x7H$_2$O—30 mg;
L-Threonine—27.8 g.

All chemicals of component 1 were mixed and dissolved in 170 mL of H$_2$O upon heating in a microwave oven. Final pH of 7 was adjusted using KOH. The obtained solution was sterilized by autoclaving.

To prepare the MM* culture medium, 170 mL of sterilized component 1 was supplemented with the stock solutions A-F (see above): A, 90 A1; B, 90 μL; C, 2 mL; D, 10 mL; E, 10 mL; F, 200 μL. Chalk (5 g) was added, and the final volume was adjusted to 200 mL using sterile water.

1.3.2. Conditions of Cultivation.

Cells of *C. glutamicum* ATCC13032/pPK4 and ATCC13032/pPK4-kbl-tdh strains grown on 2YT-agar plates (2YT-broth with bacteriological agar-agar (American type, 1.6% (w/w), Dia-m, Russian Federation, cat. No. 212303.0500f), kanamycin (50 mg/L)) were each inoculated into 4 mL of 2YT-broth (Thermo Fisher Scientific, cat. No. 22712020) supplemented with glucose (1 g/L) and kanamycin (50 mg/L), and then cultivated at 30° C. for about 6 hours. 500 μL of the resulting cell cultures were each inoculated into 4 mL of MM* medium and cultivated in 50 mL test-tubes at 30° C. for 96 hours at vigorous shaking (250 rpm).

1.3.3. Analysis of Culture Broths for Glycine and Biomass Accumulation.

40 mL of water was added into test-tubes containing culture broths obtained in Example 1.3.2, then the test-tubes were shaken vigorously to obtain suspensions. The glycine accumulated in the culture broth was determined using TLC analysis. 100 μL of resulting suspensions was each mixed with 900 μL of H$_2$O and shaken vigorously, the non-dissolved materials were removed by precipitation. 1 μL of each obtained solutions was applied onto silica gel plate and the plates were developed in the mixture of acetone: isopropanol:ammonia (25%):H$_2$O as 50:50:24:16 (v/v).

The amount of biomass accumulated in the culture broths was determined at OD$_{600}$. 100 μL of the obtained above suspensions were each mixed with 900 μL of 1.2 N HCl, and the absorption was measured at 600 nm against water.

1.4. Results.

The results of test-tube fermentations of *C. glutamicum* ATCC13032/pPK4 and ATCC13032/pPK4-kbl-tdh strains in a culture medium supplemented with L-threonine are shown in Table 1. As one can see from Table 1, the modified *C. glutamicum* ATCC13032/pPK4-kbl-tdh strain cultivated in the culture medium supplemented with 1.2 mM L-threonine, accumulated in the resulting culture broth the target glycine in amount of 0.74 mM (yield 62%). The parental *C. glutamicum* ATCC13032/pPK4 strain was not able to accumulate glycine in the culture broth.

Example 2. Production of Glycine Using a *C. glutamicum* Strain Cultivated in a Medium not Supplemented with L-Threonine 2.1. Culture Medium MM1.

The following stock solutions were used:

10×SS (salts solution) containing NH$_4$Cl (40 g/L), KH$_2$PO$_4$ (10 g/L), and K$_2$HPO$_4$ (30 g/L);

TES (trace elements solution) containing (in 100 mL) FeSO$_4$x7H$_2$O (1 g), MnSO$_4$x7H$_2$O (1 g), ZnSO$_4$x7H$_2$O (0.1 g), CoCl$_2$x6H$_2$O (0.02 g), CuSO$_4$ (0.02 g), and NiSO$_4$x6H$_2$O (0.002 g);

a)—FeSO$_4$x7H$_2$O, solution in 0.1 N HCl, 1% (w/v);
b)—MnSO$_4$x7H$_2$O, solution in water, 1% (w/v);
c)—MgSO$_4$, solution in water, 1 M;
d)—CaCl$_2$, solution in water, 1 M;
e)—Urea (Sigma), solution in water, 400 g/L;
f)—Glucose, solution in 1 N HCl, 40% (w/v), sterile;
g)—Vitamin B1, solution in water, 1.6 g/L;
h)—Vitamin B3, solution in water, 1.6 g/L;
i.—Biotin, solution in 70% (v/v) EtOH, 1 g/L;
j)—Kanamycin, solution in water, 100 g/L.

Stock solutions of 10×SS, TES, a), b), c), and d) were sterilized by autoclaving. Stock solutions of e), h), i), and j) were sterilized by filtration through a membrane 0.22 μm.

To prepare 50 mL of MM1 culture medium, the following components were mixed: 10×SS, 5 mL; TES, 50 μL; a), 50 μL; b), 10 μL; c), 250 μL; d), 10 μL; e), 250 μL; f), 1.25 mL; g), 50 μL; h), 50 μL; i), 5 μL; j), 100 μL; H$_2$O to a final volume of 50 mL.

2.2. Conditions of Cultivation.

Cells of *C. glutamicum* ATCC13032/pPK4 and ATCC13032/pPK4-kbl-tdh strains (Example 1.2) grown on 2YT-agar plates were each inoculated into 4 mL of 2YT-broth supplemented with glucose (1 g/L) and kanamycin (50 mg/L), and then cultivated at 30° C. for about 6 hours. 500 μL of the resulting cell cultures were each inoculated into 4 mL of MM1 medium and cultivated in 50 mL test-tubes at 30° C. for 24 hours at vigorous shaking (250 rpm). The glycine accumulated in the culture broth was determined using a routine HPLC analysis.

2.3. Results.

The results of test-tube fermentations of *C. glutamicum* ATCC13032/pPK4 and ATCC13032/pPK4-kbl-tdh strains in a culture medium not supplemented with L-threonine are shown in Table 2. As one can see from Table 2, the modified *C. glutamicum* ATCC13032/pPK4-kbl-tdh strain cultivated in the culture medium not supplemented with L-threonine, accumulated the target glycine in the culture broth. The parental *C. glutamicum* ATCC13032/pPK4 strain was not able to accumulate glycine in the culture broth.

TABLE 1

Results of cultivation of *C. glutamicum* strains in a culture medium supplemented with L-threonine.

| Strain | OD$_{600}$ [a] | Gly, mM [b] | Gly, mM/hour [c] |
|---|---|---|---|
| ATCC13032/pPK4 | 45 ± 1 | ND | — |
| ATCC13032/pPK4-kbl-tdh | 62 ± 1 | 737 ± 20 | 7.7 |

Data were obtained in duplicate fermentations, values are as "average ± SD" (SD - standard deviation), ND - not detected (below detection level of 10 mM):
[a] biomass accumulation;
[b] glycine concentration;
[c] productivity, calculated as concentration of glycine accumulated in the culture medium after 96 hours of cultivation.

TABLE 2

Results of cultivation of *C. glutamicum* strains in a culture medium not supplemented with L-threonine.

| Strain | OD$_{600}$ [a] | Gly, mM [b] |
|---|---|---|
| ATCC13032/pPK4 | 17 ± 0.5 | ND |
| ATCC13032/pPK4-kbl-tdh | 17 ± 0.5 | 320 ± 20 |

Conditions of cultivation: glucose, 10 g/L; culturing time, 24 hours; temperature, 30° C. Data were obtained in triplicate fermentations, values are as "average ± SD" (SD - standard deviation), ND - not detected (below detection level of 10 mg/L):
[a] biomass accumulation;
[b] glycine concentration.

Example 3. Production of Glycine Using an E. coli Strain Cultivated in a Medium Supplemented with L-Threonine 3.1. Construction of E. coli MG1655/pET15(b+) and MG1655/pEL-kbl-tdh strains.

Figure 4:
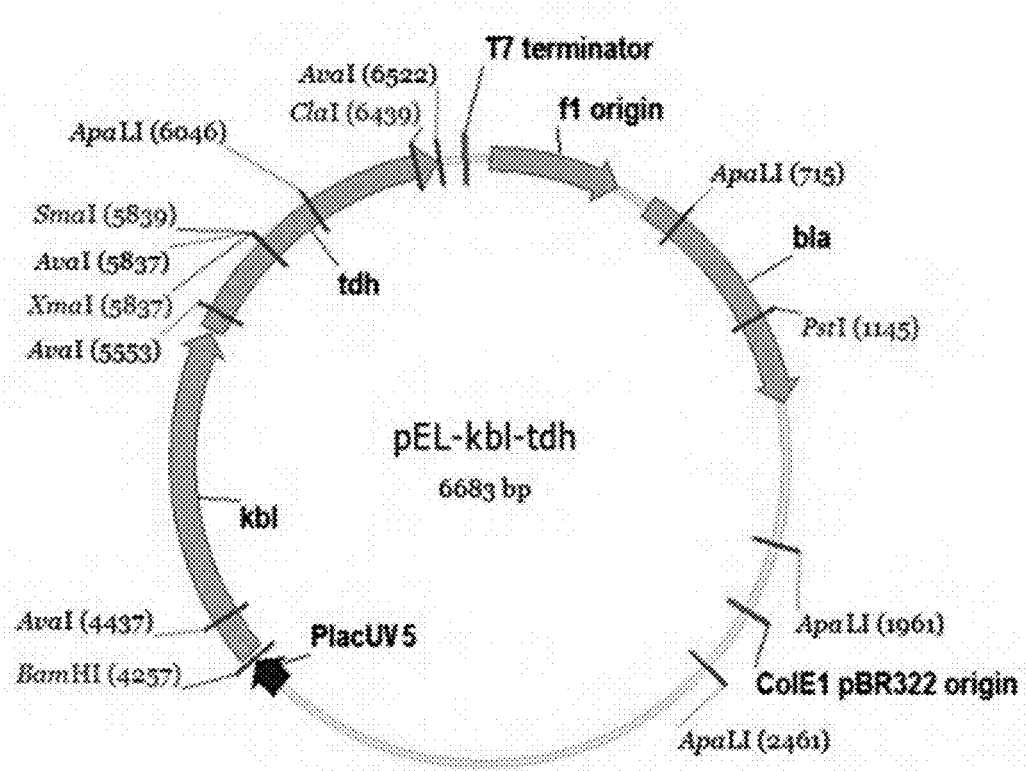
FIG. 4 shows the physical map of pEL-kbl-tdh plasmid.

A DNA fragment of chromosome of the E. coli MG1655 strain (ATCC 47076) was amplified using primers P1 (SEQ ID NO: 7) and P2 (SEQ ID NO: 8), and the chromosome of E. coli MG1655 as a template. The obtained DNA fragment (2277 bp) was digested using restrictases BamHI and NotI and cloned into the vector obtained after the digestion of pEL-IDO(Lys, 23) plasmid (WO2009082029 A1) with the same restrictases. As a result, the <kbl-tdh> operon native to E. coli MG1655 was placed under the control of $P_{lacUV5}$ promoter on the multicopy plasmid (FIG. 4). Thus, the strain E. coli MG1655/pEL-kbl-tdh was constructed. As a control strain, the E. coli MG1655 strain was constructed by introducing the pET-15(b+) vector (Novagen, Germany).

3.2. Cultivation of E. coli MG1655/pET15(b+) and MG1655/pEL-kbl-tdh strain.

Cells of E. coli MG1655/pEL-kbl-tdh and MG1655/pET15(b+) strains (Example 3.1) grown on Luria-Bertani (LB)-agar plates (LB-broth Powder (Thermo Fisher Scientific, cat. No. 12780029), bacteriological agar-agar (American type, 1.6% (w/w)), kanamycin (50 mg/L)) were each inoculated into 4 mL of 2YT-broth supplemented with glucose (1 g/L) and kanamycin (100 mg/L), and then cultivated at 37° C. for about 6 hours. 40 µL of the resulting cells cultures were each inoculated into 4 mL of M9-salts medium (Sigma, M6030) supplemented with glucose (4 g/L) and L-threonine (100 mM) and cultivated in 50 mL test-tubes at 37° C. for 48 hours at vigorous shaking (250 rpm). The glycine accumulated in the culture broth was determined using a routine HPLC analysis.

3.3. Results.

The results of test-tube fermentations of E. coli MG1655/pEL-kbl-tdh and MG1655/pET15(b+) strains in a culture medium supplemented with L-threonine are shown in Table 3. As one can see from Table 3, the modified E. coli MG1655/pEL-kbl-tdh strain cultivated in the culture medium supplemented with 100 mM L-threonine, accumulated in the resulting culture broth the target glycine in amount of 26 mM (yield 26%). The non-modified E. coli MG1655/pET15(b+) strain was not able to accumulate glycine in the culture broth.

TABLE 3

Results of cultivation of E. coli strains in a culture medium supplemented with L-threonine.

| Strain | $OD_{600}$ [a] | Gly, g/L [b] |
|---|---|---|
| MG1655/pET15(b+) | 5 | ND |
| MG1655/pEL-kbl-tdh | 5 | 3.1 ± 0.1 |

Data were obtained in duplicate fermentations, values are as "average ± SD" (SD - standard deviation), ND - not detected (below detection level of 10 mg/L):
[a] biomass accumulation;
[b] glycine concentration.

Example 4. Production of Glycine Using an E. coli Strain Cultivated in a Medium not Supplemented with L-Threonine 4.1. Culture Medium MM2.
The following stock solutions were used:
10×SS (salts solution) containing $NH_4Cl$ (40 g/L), $KH_2PO_4$ (10 g/L), and $K_2HPO_4$ (30 g/L);
A'—$FeSO_4 \times 7H_2O$, solution in 0.1 N HCl, 1% (w/v);
B'— $MnSO_4 \times 7H_2O$, solution in water, 1% (w/v);
C'— $MgSO_4$, solution in water, 1 M;
D'—$CaCl_2$, solution in water, 1 M;
E'—Glucose, solution in 1 N HCl, 40% (w/v), sterile;
F'— Vitamin B1, solution in water, 1.6 g/L;
G'—Biotin, solution in 70% (v/v) EtOH, 1 g/L;
H'— Kanamycin, solution in water, 50 g/L;
I'— 2-YT culture broth solution;
J'—L-Threonine, solution in water, 1 M.
Stock solutions of 10×SS, A', B', C', and D' were sterilized by autoclaving. Stock solutions of E', F', G', H', and J' were sterilized by filtration through a membrane 0.22 µm.
To prepare 50 mL of MM2 culture medium, the following components were mixed: 10×SS, 5 mL; A', 50 µL; B', 10 µL; C', 250 µL; D', 10 µL; E', 1.25 mL; F', 80 µL; G', 5 µL; H', 100 µL; I', 2.5 mL; J', 5 mL; $H_2O$ to a final volume of 50 mL.

4.2. Cultivation Conditions.

Cells of E. coli MG1655/pEL-kbl-tdh and MG1655/pET15(b+) strains (Example 3.1) grown on 2YT-agar plates were each inoculated into 4 mL of 2YT-broth supplemented with glucose (1 g/L) and kanamycin (50 mg/L), and then cultivated at 37° C. for about 6 hours. 40 µL of the resulting cells cultures were each inoculated into 4 mL of MM2 medium and cultivated in 50 mL test-tubes at 37° C. for 48 hours at vigorous shaking (250 rpm). The glycine accumulated in the culture broth was determined using a routine HPLC analysis.

4.3. Results.

The results of test-tube fermentation of E. coli MG1655/pEL-kbl-tdh and MG1655/pET15(b+) strains in a culture medium not supplemented with L-threonine are shown in Table 4. As one can see from the Table 4, the modified E. coli MG1655/pEL-kbl-tdh strain cultivated in the culture medium not supplemented with L-threonine, accumulated the target glycine in the culture broth. The non-modified E. coli MG1655/pET15(b+) strain was not able to accumulate glycine in the culture broth.

TABLE 4

Results of cultivation of E. coli strains in a culture medium not supplemented with L-threonine.

| Strain | $OD_{600}$ [a] | Gly, mg/L [b] |
|---|---|---|
| MG1655/pET15(b+) | 5 | ND |
| MG1655/pEL-kbl-tdh | 5 | 110 ± 10 |

Conditions of cultivation: glucose, 10 g/L; culturing time, 48 hours; temperature, 37° C.
Data were obtained in triplicate fermentations, values are as "average ± SD" (SD - standard deviation), ND - not detected (below detection level of 10 mg/L):
[a] biomass accumulation;
[b] glycine concentration.

INDUSTRIAL APPLICABILITY

The method of the present invention is useful for the production of glycine by fermentation of a bacterium.

While the invention has been described in detail with reference to preferred embodiments thereof, it will be apparent to the one of ordinary skill in the art that various changes can be made, and equivalents employed, without departing from the scope of the invention.

What is claimed is:

1. A method for producing glycine or a salt thereof comprising:
   (i) cultivating a glycine-producing bacterium in a culture medium to produce and accumulate the glycine or a salt thereof in the culture medium, and
   (ii) collecting the glycine or the salt thereof from the culture medium;
   wherein the bacterium has been modified to overexpress a gene encoding a protein having L-threonine 3-dehydrogenase activity and a gene encoding a protein having 2-amino-3-oxobutanoate coenzyme A ligase activity,
   wherein said bacterium belongs to the genus *Corynebacterium*, and
   wherein said protein having L-threonine 3-dehydrogenase activity is selected from the group consisting of:
   (A) a protein comprising the amino acid sequence shown in SEQ ID NO: 2,
   (B) a protein comprising the amino acid sequence shown in SEQ ID NO: 2, but which includes substitution, deletion, insertion, and/or addition of 1 to 50 amino acid residues, and wherein said protein has L-threonine 3-dehydrogenase activity,
   (C) a protein having an identity of amino acid residues of not less than 90% with respect to the entire amino acid sequence shown in SEQ ID NO: 2, and wherein said protein has L-threonine 3-dehydrogenase activity;
   and wherein said protein having 2-amino-3-oxobutanoate coenzyme A ligase activity is selected from the group consisting of:
   (D) a protein comprising the amino acid sequence shown in SEQ ID NO: 4,
   (E) a protein comprising the amino acid sequence shown in SEQ ID NO: 4, but which includes substitution, deletion, insertion, and/or addition of 1 to 50 amino acid residues, and wherein said protein has 2-amino-3-oxobutanoate coenzyme A ligase activity,
   (F) a protein having an identity of amino acid residues of not less than 90% with respect to the entire amino acid sequence shown in SEQ ID NO: 4, and wherein said protein has 2-amino-3-oxobutanoate coenzyme A ligase activity.

2. The method according to claim 1, wherein said protein having L-threonine 3-dehydrogenase activity is encoded by a tdh gene and said protein having 2-amino-3-oxobutanoate coenzyme A ligase activity is encoded by a kbl gene.

3. The method according to claim 1, wherein said protein having L-threonine 3-dehydrogenase activity is encoded by a DNA selected from the group consisting of:
   (a) a DNA comprising the nucleotide sequence shown in SEQ ID NO: 1,
   (b) a DNA encoding a protein comprising the amino acid sequence shown in SEQ ID NO: 2, but which includes substitution, deletion, insertion, and/or addition of 1 to 50 amino acid residues, and wherein said protein has L-threonine 3-dehydrogenase activity,
   (c) a DNA which is a variant nucleotide sequence of SEQ ID NO: 1 due to the degeneracy of the genetic code;
   and wherein said protein having 2-amino-3-oxobutanoate coenzyme A ligase is encoded by a DNA selected from the group consisting of:
   (d) a DNA comprising the nucleotide sequence shown in SEQ ID NO: 3,
   (e) a DNA encoding a protein comprising the amino acid sequence shown in SEQ ID NO: 4, but which includes substitution, deletion, insertion and/or addition of 1 to 50 amino acid residues, and wherein said protein has 2-amino-3-oxobutanoate coenzyme A ligase activity,
   (f) a DNA which is a variant nucleotide sequence of SEQ ID NO: 3 due to the degeneracy of the genetic code.

4. The method according to claim 1, wherein the gene encoding the protein having L-threonine 3-dehydrogenase activity and the gene encoding the protein having 2-amino-3-oxobutanoate coenzyme A ligase activity are overexpressed by introducing the genes, increasing the copy number of the genes, modifying an expression regulatory region of the genes, or a combination of these;
   so that the expression of said genes is enhanced as compared with a non-modified bacterium.

5. A glycine-producing bacterium, wherein said bacterium has been modified to overexpress a gene encoding a protein having L-threonine 3-dehydrogenase activity and a gene encoding a protein having 2-amino-3-oxobutanoate coenzyme A ligase activity,
   wherein said bacterium belongs to the genus *Corynebacterium*, and
   wherein said protein having L-threonine 3-dehydrogenase activity is selected from the group consisting of:
   (A) a protein comprising the amino acid sequence shown in SEQ ID NO: 2,
   (B) a protein comprising the amino acid sequence shown in SEQ ID NO: 2, but which includes substitution, deletion, insertion, and/or addition of 1 to 50 amino acid residues, and wherein said protein has L-threonine 3-dehydrogenase activity,
   (C) a protein having an identity of amino acid residues of not less than 90% with respect to the entire amino acid sequence shown in SEQ ID NO: 2, and wherein said protein has L-threonine 3-dehydrogenase activity;
   and wherein said protein having 2-amino-3-oxobutanoate coenzyme A ligase activity is selected from the group consisting of:
   (D) a protein comprising the amino acid sequence shown in SEQ ID NO: 4,
   (E) a protein comprising the amino acid sequence shown in SEQ ID NO: 4, but which includes substitution, deletion, insertion, and/or addition of 1 to 50 amino acid residues, and wherein said protein has 2-amino-3-oxobutanoate coenzyme A ligase activity, (F) a protein having an identity of amino acid residues of not less than 90% with respect to the entire amino acid sequence shown in SEQ ID NO: 4, and wherein said protein has 2-amino-3-oxobutanoate coenzyme A ligase activity.

6. The bacterium according to claim 5, wherein said bacterium has been modified to overexpress a tdh gene and a kbl gene.

7. The bacterium according to claim 5, wherein the gene encoding the protein having L-threonine 3-dehydrogenase activity and the gene encoding the protein having 2-amino-3-oxobutanoate coenzyme A ligase activity are overexpressed by introducing the genes, increasing the copy number of the genes, modifying an expression regulatory region of the genes, or a combination of these;

so that the expression of said genes is enhanced as compared with a non-modified bacterium.

* * * * *

SEQUENCE LISTING

<160> NUMBER OF SEQ ID NOS: 8

<210> SEQ ID NO 1
<211> LENGTH: 1026
<212> TYPE: DNA
<213> ORGANISM: Escherichia coli

<400> SEQUENCE: 1

```
atgaaagcgt tatccaaact gaaagcggaa gagggcatct ggatgaccga cgttcctgta      60
ccggaactcg ggcataacga tctgctgatt aaaatccgta aaacagccat ctgcgggact     120
gacgttcaca tctataactg ggatgagtgg tcgcaaaaaa ccatcccggt gccgatggtc     180
gtgggccatg aatatgtcgg tgaagtggta ggtattggtc aggaagtgaa aggcttcaag     240
atcggcgatc gcgtttctgg cgaaggccat atcacctgtg gtcattgccg caactgtcgt     300
ggtggtcgta cccatttgtg ccgcaacacg ataggcgttg gtgttaatcg cccgggctgc     360
tttgccgaat atctggtgat cccggcattc aacgccttca aatccccga caatatttcc      420
gatgacttag ccgcaatttt tgatcccttc ggtaacgccg tgcataccgc gctgtcgttt     480
gatctggtgg gcgaagatgt gctggtttct ggtgcaggcc cgattggtat tatggcagcg     540
gcggtggcga acacgttgg tgcacgcaat gtggtgatca ctgatgttaa cgaataccgc     600
cttgagctgg cgcgtaaaat gggtatcacc cgtgcggtta acgtcgccaa agaaaatctc     660
aatgacgtga tggcggagtt aggcatgacc gaaggttttg atgtcggtct ggaaatgtcc     720
ggtgcgccgc cagcgtttcg taccatgctt gacaccatga atcacggcgg ccgtattgcg     780
atgctgggta ttccgccgtc tgatatgtct atcgactgga ccaaagtgat ctttaaaggc     840
ttgttcatta aagtatttta cggtcgtgag atgtttgaaa cctggtacaa gatggcggcg     900
ctgattcagt ctggcctcga tctttcgccg atcattaccc atcgtttctc tatcgatgat     960
ttccagaagg gctttgacgc tatgcgttcg ggccagtccg ggaaagttat tctgagctgg    1020
gattaa                                                                1026
```

<210> SEQ ID NO 2
<211> LENGTH: 341
<212> TYPE: PRT
<213> ORGANISM: Escherichia coli

<400> SEQUENCE: 2

```
Met Lys Ala Leu Ser Lys Leu Lys Ala Glu Glu Gly Ile Trp Met Thr
1               5                   10                  15

Asp Val Pro Val Pro Glu Leu Gly His Asn Asp Leu Leu Ile Lys Ile
            20                  25                  30

Arg Lys Thr Ala Ile Cys Gly Thr Asp Val His Ile Tyr Asn Trp Asp
        35                  40                  45

Glu Trp Ser Gln Lys Thr Ile Pro Val Pro Met Val Val Gly His Glu
    50                  55                  60

Tyr Val Gly Glu Val Val Gly Ile Gly Gln Glu Val Lys Gly Phe Lys
65                  70                  75                  80

Ile Gly Asp Arg Val Ser Gly Glu Gly His Ile Thr Cys Gly His Cys
                85                  90                  95

Arg Asn Cys Arg Gly Gly Arg Thr His Leu Cys Arg Asn Thr Ile Gly
            100                 105                 110

Val Gly Val Asn Arg Pro Gly Cys Phe Ala Glu Tyr Leu Val Ile Pro
        115                 120                 125

Ala Phe Asn Ala Phe Lys Ile Pro Asp Asn Ile Ser Asp Asp Leu Ala
```

```
                130             135              140
Ala Ile Phe Asp Pro Phe Gly Asn Ala Val His Thr Ala Leu Ser Phe
145                 150                 155                 160

Asp Leu Val Gly Glu Asp Val Leu Val Ser Gly Ala Gly Pro Ile Gly
                165                 170                 175

Ile Met Ala Ala Val Ala Lys His Val Gly Ala Arg Asn Val Val
                180                 185                 190

Ile Thr Asp Val Asn Glu Tyr Arg Leu Glu Leu Ala Arg Lys Met Gly
                195                 200                 205

Ile Thr Arg Ala Val Asn Val Ala Lys Glu Asn Leu Asn Asp Val Met
            210                 215                 220

Ala Glu Leu Gly Met Thr Glu Gly Phe Asp Val Gly Leu Glu Met Ser
225                 230                 235                 240

Gly Ala Pro Pro Ala Phe Arg Thr Met Leu Asp Thr Met Asn His Gly
                245                 250                 255

Gly Arg Ile Ala Met Leu Gly Ile Pro Pro Ser Asp Met Ser Ile Asp
                260                 265                 270

Trp Thr Lys Val Ile Phe Lys Gly Leu Phe Ile Lys Gly Ile Tyr Gly
                275                 280                 285

Arg Glu Met Phe Glu Thr Trp Tyr Lys Met Ala Ala Leu Ile Gln Ser
                290                 295                 300

Gly Leu Asp Leu Ser Pro Ile Ile Thr His Arg Phe Ser Ile Asp Asp
305                 310                 315                 320

Phe Gln Lys Gly Phe Asp Ala Met Arg Ser Gly Gln Ser Gly Lys Val
                325                 330                 335

Ile Leu Ser Trp Asp
            340

<210> SEQ ID NO 3
<211> LENGTH: 1197
<212> TYPE: DNA
<213> ORGANISM: Escherichia coli

<400> SEQUENCE: 3
atgcgtggag aattttatca gcagttaacc aacgatctgg aaaccgcacg ggcggaaggg    60
ttgtttaaag aagagcgcat tattacgtct gcgcagcaag cagatatcac tgtggctgat   120
ggaagccacg tcattaactt tgtgccaac aactatctcg gctggcgaa tcatcctgat    180 ctgattgcgg cggcaaaggc gggaatggat tctcacggtt tcggcatggc ttcggtgcgt   240
tttatttgcg gcactcagga cagccataaa gagcttgaac aaaaactggc ggccttcctg   300
gggatggaag atgcgattct ctactcttcc tgctttgatg ctaacggtgg cctgtttgaa   360
acgcttctgg gtgcggaaga cgccattatc tccgacgcac tgaaccacgc gtctattatt   420
gatggtgtgc gtctgtgcaa agctaaacgc tatcgctatg ccaacaacga tatgcaggag   480
ctggaagcac gtctgaaaga gcgcgtgaa gccgtgcgc gtcatgtgct gatcgccacc    540
gatggtgtgt ctcaatgga cggcgtgatt gccaacctga agggcgtttg cgatctggca   600
gataaatatg atgccctggt gatggtagac gactcccacg cggtcggttt tgtcggtgaa   660
aatggtcgtg gttcccatga atactgcgat gtgatgggcc gggtcgatat tatcaccggt   720
acgcttggta aagcgctggg cggggcttct ggtggttata ccgcggcgcg caagaagtg    780 gttgagtggc tgcgcagcg ttctcgtccg tacctgttct ccaactcgct ggcaccggcc   840
attgttgccg cgtccatcaa agtactggag atggtcgaag cgggcagcga actgcgtgac   900
```

```
cgtctgtggg cgaacgcgcg tcagttccgt gagcaaatgt cggcggcggg ctttacccty    960
gcgggagccg atcacgccat tattccggtc atgcttggtg atgcggtagt ggcgcagaaa   1020
tttgcccgtg agctgcaaaa agagggcatt tacgttaccg gtttcttcta tccggtcgtt   1080
ccgaaaggtc aggcgcgtat tcgtacccag atgtctgcgg cgcataccc tgagcaaatt   1140 acgcgtgcag tagaagcatt tacgcgtatt ggtaaacaac tgggcgttat cgcctga     1197
```

<210> SEQ ID NO 4
<211> LENGTH: 398
<212> TYPE: PRT
<213> ORGANISM: Escherichia coli

<400> SEQUENCE: 4

```
Met Arg Gly Glu Phe Tyr Gln Gln Leu Thr Asn Asp Leu Glu Thr Ala
1               5                   10                  15

Arg Ala Glu Gly Leu Phe Lys Glu Arg Ile Ile Thr Ser Ala Gln
            20                  25                  30

Gln Ala Asp Ile Thr Val Ala Asp Gly Ser His Val Ile Asn Phe Cys
        35                  40                  45

Ala Asn Asn Tyr Leu Gly Leu Ala Asn His Pro Asp Leu Ile Ala Ala
    50                  55                  60

Ala Lys Ala Gly Met Asp Ser His Gly Phe Gly Met Ala Ser Val Arg
65                  70                  75                  80

Phe Ile Cys Gly Thr Gln Asp Ser His Lys Glu Leu Glu Gln Lys Leu
                85                  90                  95

Ala Ala Phe Leu Gly Met Glu Asp Ala Ile Leu Tyr Ser Ser Cys Phe
            100                 105                 110

Asp Ala Asn Gly Gly Leu Phe Glu Thr Leu Leu Gly Ala Glu Asp Ala
        115                 120                 125

Ile Ile Ser Asp Ala Leu Asn His Ala Ser Ile Ile Asp Gly Val Arg
    130                 135                 140

Leu Cys Lys Ala Lys Arg Tyr Arg Tyr Ala Asn Asn Asp Met Gln Glu
145                 150                 155                 160

Leu Glu Ala Arg Leu Lys Glu Ala Arg Glu Ala Gly Ala Arg His Val
                165                 170                 175

Leu Ile Ala Thr Asp Gly Val Phe Ser Met Asp Gly Val Ile Ala Asn
            180                 185                 190

Leu Lys Gly Val Cys Asp Leu Ala Asp Lys Tyr Asp Ala Leu Val Met
        195                 200                 205

Val Asp Asp Ser His Ala Val Gly Phe Val Gly Glu Asn Gly Arg Gly
    210                 215                 220

Ser His Glu Tyr Cys Asp Val Met Gly Arg Val Asp Ile Ile Thr Gly
225                 230                 235                 240

Thr Leu Gly Lys Ala Leu Gly Gly Ala Ser Gly Gly Tyr Thr Ala Ala
                245                 250                 255

Arg Lys Glu Val Val Glu Trp Leu Arg Gln Arg Ser Arg Pro Tyr Leu
            260                 265                 270

Phe Ser Asn Ser Leu Ala Pro Ala Ile Val Ala Ala Ser Ile Lys Val
        275                 280                 285

Leu Glu Met Val Glu Ala Gly Ser Glu Leu Arg Asp Arg Leu Trp Ala
    290                 295                 300

Asn Ala Arg Gln Phe Arg Glu Gln Met Ser Ala Ala Gly Phe Thr Leu
305                 310                 315                 320

Ala Gly Ala Asp His Ala Ile Ile Pro Val Met Leu Gly Asp Ala Val
```

```
                    325                 330                 335
Val Ala Gln Lys Phe Ala Arg Glu Leu Gln Lys Glu Gly Ile Tyr Val
                340                 345                 350

Thr Gly Phe Phe Tyr Pro Val Val Pro Lys Gly Gln Ala Arg Ile Arg
            355                 360                 365

Thr Gln Met Ser Ala Ala His Thr Pro Glu Gln Ile Thr Arg Ala Val
        370                 375                 380

Glu Ala Phe Thr Arg Ile Gly Lys Gln Leu Gly Val Ile Ala
385                 390                 395

<210> SEQ ID NO 5
<211> LENGTH: 1456
<212> TYPE: DNA
<213> ORGANISM: Artificial Sequence
<220> FEATURE:
<223> OTHER INFORMATION: artificial DNA-fragment <KBL>

<400> SEQUENCE: 5
tctagataca ggacgtcatt tcgtacgata agggccctag ccctcgaggt gtaaggtaga      60
caatcgcgtg ttttttaagc atgctcaaaa tcattcatcc ccggtggccc ggttacgtaa     120
agatcggcaa agatgatcaa ctaaagcgat catctgaagt tgtagcggga ccgagcatcc     180
ggacggttac tagtggggtt tcatcgtccc agttgtggcc ggtaacaagg aagcaggttt     240
acatatgcgt ggagaatttt atcagcagtt aaccaacgat ctggaaaccg cacgggcgga     300
agggttgttt aaagaagagc gcattattac gtctgcgcag caagcagata tcactgtggc     360
tgatggaagc cacgtcatta actttgtgc caacaactat ctcgggctgg cgaatcatcc     420
tgatctgatt gcggcggcaa aggcgggaat ggattctcac ggtttcggca tggcttcggt     480
gcgttttatt tgcggcactc aggacagcca taaagagctt gaacaaaaac tggcggcctt     540
cctggggatg aagatgcga ttctctactc ttcctgcttt gatgctaacg gtggcctgtt     600
tgaaacgctt ctgggtgcgg aagacgccat tatctccgac gcactgaacc acgcgtctat     660
tattgatggt gtgcgtctgt gcaaagctaa acgctatcgc tatgccaaca cgatatgca     720 ggagctggaa gcacgtctga agaagcgcg tgaagccggt gcgcgtcatg tgctgatcgc     780
caccgatggt gtgttctcaa tggacggcgt gattgccaac ctgaagggcg tttgcgatct     840
ggcagataaa tatgatgccc tggtgatggt agacgactcc cacgcggtcg gttttgtcgg     900
tgaaaatggt cgtggttccc atgaatactg cgatgtgatg ggccgggtcg atattatcac     960
cggtacgctt ggtaaagcgc tgggcggggc ttctggtggt tataccgcgg cgcgcaaaga    1020
agtggttgag tggctgcgcc agcgttctcg tccgtacctg ttctccaact cgctggcacc    1080
ggccattgtt gccgcgtcca tcaaagtact ggagatggtc gaagcgggca gcgaactgcg    1140
tgaccgtctg tgggcgaacg cgcgtcagtt ccgtgagcaa atgtcggcgg cgggctttac    1200
cctggcggga gccgatcacg ccattattcc ggtcatgctt ggtgatgcgg tagtggcgca    1260
gaaatttgcc cgtgagctgc aaaaagaggg catttacgtt accggtttct ctatccggt     1320 cgttccgaaa ggtcaggcgc gtattcgtac ccagatgtct gcggcgcata cccctgagca    1380
aattacgcgt gcagtagaag catttacgcg tattggtaaa caactgggcg ttatcgcctg    1440
aggcgcctca gctagc                                                   1456

<210> SEQ ID NO 6
<211> LENGTH: 1506
<212> TYPE: DNA
<213> ORGANISM: Artificial Sequence
```

<220> FEATURE:
<223> OTHER INFORMATION: artificial DNA-fragment <TDH>

<400> SEQUENCE: 6

```
gctagcatta gatctatctg agactttact ttgtggattc acggggtgt agtgcaattc      60
ataattagcc ccattcgggg gagcagatcg cggcgcgaac gatttcaggt tcgttccctg    120
caaaaactat ttagcgcaag tgttggaaat gcccccgtct ggggtcaatg tctattttg     180
aatgtgtttg tatgattttg aatccgctgc aaaatctttg ttccccgct aaagttgggg    240
acaggttgac acggagttga ctcgacgaat tatccaatgt gagtaggttt ggtgcgtgag   300
ttggaaaatt tcgccatact cgcccttggg ttctgtcagc tcaagaattc ttgagtgacc   360
gatgctctga ttgacctaac tgcttgacac attgcatttc ctacaatctt tagaggagac   420
accatatgaa agcgttatcc aaactgaaag cggaagaggg catctggatg accgacgttc   480
ctgtaccgga actcgggcat aacgatctgc tgattaaaat ccgtaaaaca gccatctgcg   540
ggactgacgt tcacatctat aactgggatg agtggtcgca aaaaaccatc ccggtgccga   600
tggtcgtggg ccatgaatat gtcggtgaag tggtaggtat tggtcaggaa gtgaaaggct   660
tcaagatcgg cgatcgcgtt tctggcgaag gccatatcac ctgtggtcat tgccgcaact   720
gtcgtggtgg tcgtacccat ttgtgccgca acacgatagg cgttggtgtt aatcgcccgg   780
gctgctttgc cgaatatctg gtgatcccgg cattcaacgc cttcaaaatc cccgacaata   840
tttccgatga cttagccgca attttttgatc ccttcggtaa cgccgtgcat accgcgctgt   900
cgtttgatct ggtgggcgaa gatgtgctgg tttctggtgc aggcccgatt ggtattatgg   960
cagcggcggt ggcgaaacac gttggtgcac gcaatgtggt gatcactgat gttaacgaat  1020
accgccttga gctggcgcgt aaaatgggta tcacccgtgc ggttaacgtc gccaaagaaa  1080
atctcaatga cgtgatggcg gagttaggca tgaccgaagg ttttgatgtc ggtctggaaa  1140
tgtccggtgc gccgccagcg tttcgtacca tgcttgacac catgaatcac ggcggccgta  1200
ttgcgatgct gggtattccg ccgtctgata tgtctatcga ctggaccaaa gtgatcttta  1260
aaggcttgtt cattaaaggt atttacggtc gtgagatgtt tgaaacctgg tacaagatgg  1320
cggcgctgat tcagtctggc ctcgatcttt cgccgatcat tacccatcgt ttctctatcg  1380
atgatttcca gaagggcttt gacgctatgc gttcgggcca gtccgggaaa gttattctga  1440
gctgggatta agcggccgca gctgtacaat gtccggacta tcctgcagga atcctaggga  1500
gtcgac                                                             1506
```

<210> SEQ ID NO 7
<211> LENGTH: 70
<212> TYPE: DNA
<213> ORGANISM: Artificial Sequence
<220> FEATURE:
<223> OTHER INFORMATION: primer P1

<400> SEQUENCE: 7

```
tctagaggat cctcaagaag gagatataca atgcgtggag aatttatca gcagttaacc    60
aacgatctgg                                                           70
```

```
<210> SEQ ID NO 8
<211> LENGTH: 46
<212> TYPE: DNA
<213> ORGANISM: Artificial Sequence
<220> FEATURE:
<223> OTHER INFORMATION: primer P2

<400> SEQUENCE: 8
ctcgagtgcg gccgcttaat cccagctcag aataactttc ccggac                46
```